(12) United States Patent
Nistor

(10) Patent No.: US 11,666,522 B2
(45) Date of Patent: Jun. 6, 2023

(54) USE OF CELL MEMBRANE-BOUND SIGNALING FACTORS

(71) Applicant: AiVita Biomedical, Inc., Irvine, CA (US)

(72) Inventor: Gabriel Nistor, Irvine, CA (US)

(73) Assignee: AIVITA BIOMEDICAL, INC., Irvine, CA (US)

( * ) Notice: Subject to any disclaimer, the term of this patent is extended or adjusted under 35 U.S.C. 154(b) by 101 days.

(21) Appl. No.: 16/763,959

(22) PCT Filed: Nov. 16, 2018

(86) PCT No.: PCT/US2018/061550
§ 371 (c)(1),
(2) Date: May 13, 2020

(87) PCT Pub. No.: WO2019/099850
PCT Pub. Date: May 23, 2019

(65) Prior Publication Data
US 2021/0379200 A1 Dec. 9, 2021

Related U.S. Application Data

(60) Provisional application No. 62/587,338, filed on Nov. 16, 2017.

(51) Int. Cl.
*A61K 38/17* (2006.01)
*A61K 47/40* (2006.01)
(Continued)

(52) U.S. Cl.
CPC ............... *A61K 8/738* (2013.01); *A61K 8/64* (2013.01); *A61K 9/0014* (2013.01); *A61K 9/08* (2013.01);
(Continued)

(58) Field of Classification Search
CPC .... A61K 38/1709; A61K 47/26; A61K 47/40; A61K 47/51; A61K 47/69; C07K 1/145;
(Continued)

(56) References Cited

U.S. PATENT DOCUMENTS 6,207,718 B1 * 3/2001 Papadimitriou ... A61K 38/1703
514/772.3
2002/0004061 A1 1/2002 Panayotatos et al.
(Continued)

FOREIGN PATENT DOCUMENTS

CN 1306436 A 8/2001
CN 103781799 A 5/2014
(Continued)

OTHER PUBLICATIONS

Guimaraes et al. Potent in vivo lung cancer Wnt signaling inhibition via cyclodextrin-LGK974 inclusion complexes. Journal of Controlled Release. Oct. 2, 2018, vol. 290, pp. 75-87. (Year: 2018).*
(Continued)

*Primary Examiner* — Jeffrey E. Russel
(74) *Attorney, Agent, or Firm* — Wilson Sonsini Goodrich & Rosati

(57) ABSTRACT

Disclosed herein are compositions comprising complexes of cyclodextrins and lipid-modified stem cell proteins. Also disclosed are topical compositions the complexes. Methods of using the compositions for the therapeutic purposes are also disclosed as well as methods of producing the compositions.

24 Claims, 21 Drawing Sheets

(51) Int. Cl.
| | |
|---|---|
| *C07K 14/47* | (2006.01) |
| *C12N 5/0735* | (2010.01) |
| *C12N 5/074* | (2010.01) |
| *A61K 8/73* | (2006.01) |
| *A61K 47/61* | (2017.01) |
| *A61K 47/54* | (2017.01) |
| *A61K 47/69* | (2017.01) |
| *A61K 8/64* | (2006.01) |
| *A61K 9/00* | (2006.01) |
| *A61K 9/08* | (2006.01) |
| *A61K 38/18* | (2006.01) |
| *A61K 47/26* | (2006.01) |
| *A61Q 7/00* | (2006.01) |
| *C12N 5/00* | (2006.01) |

(52) U.S. Cl.
CPC .......... *A61K 38/1709* (2013.01); *A61K 38/18* (2013.01); *A61K 47/26* (2013.01); *A61K 47/40* (2013.01); *A61K 47/543* (2017.08); *A61K 47/61* (2017.08); *A61K 47/6951* (2017.08); *A61Q 7/00* (2013.01); *C07K 14/4705* (2013.01); *C12N 5/0018* (2013.01); *C12N 5/0606* (2013.01); *C12N 5/0607* (2013.01); *A61K 2800/56* (2013.01); *C12N 2500/34* (2013.01)

(58) Field of Classification Search
CPC ................ C07K 14/47; C07K 14/4702; C07K 14/4705; C07K 14/82; C12N 5/0018; C12N 5/0606; C12N 5/0607; C12N 5/16; C12N 2500/34
See application file for complete search history.

(56) References Cited

U.S. PATENT DOCUMENTS

| | | | |
|---|---|---|---|
| 2002/0032161 | A1 | 3/2002 | Ringshaw et al. |
| 2007/0053883 | A1* | 3/2007 | Beachy ................ C12N 5/0619 514/1.2 |
| 2009/0203134 | A1 | 8/2009 | Takahashi et al. |
| 2009/0304635 | A1 | 12/2009 | Cotsarelis et al. |
| 2010/0184033 | A1 | 7/2010 | West et al. |
| 2011/0237540 | A1 | 9/2011 | Crawford et al. |
| 2012/0121693 | A1 | 5/2012 | Cotsarelis et al. |
| 2012/0143084 | A1 | 6/2012 | Shoham |
| 2013/0310963 | A1 | 11/2013 | Davison |
| 2014/0309157 | A1 | 10/2014 | Chung et al. |
| 2016/0354169 | A1 | 12/2016 | Suttin et al. |
| 2019/0358145 | A1 | 11/2019 | Nistor |
| 2020/0390678 | A1 | 12/2020 | Nistor |

FOREIGN PATENT DOCUMENTS

| | | | |
|---|---|---|---|
| EP | 0978285 | A1 | 2/2000 |
| EP | 1844787 | A1 | 10/2007 |
| WO | WO-9920298 | A1 | 4/1999 |
| WO | 2001/074164 | A1 | 10/2001 |
| WO | 2003/102215 | A2 | 12/2003 |
| WO | WO-2006072016 | A2 | 7/2006 |
| WO | WO-2006105109 | A2 | 10/2006 |
| WO | WO-2009058399 | A1 | 5/2009 |
| WO | 2010/056759 | A1 | 5/2010 |
| WO | WO-2013018976 | A1 | 2/2013 |
| WO | WO-2013040309 | A2 | 3/2013 |
| WO | WO-2014172561 | A1 | 10/2014 |
| WO | 2018/094100 | A1 | 5/2018 |
| WO | 2019/099850 | A1 | 5/2019 |
| WO | 2019/099861 | A1 | 5/2019 |

OTHER PUBLICATIONS

Challa et al., Cyclodextrins in drug delivery: an updated review. AAPS PharmSciTech, vol. 6, No. 2, pp. e329-e357 (2005).
Fathke et al., Wnt signaling induces epithelial differentiation during cutaneous wound healing. BMC Cell Biology, vol. 7, No. 4; 9 pages (2006).
International Search Report and Written Opinion, dated Feb. 11, 2019, for PCT International Application Serial No. PCT/US18/61563 filed on Nov. 16, 2018.
International Search Report and Written Opinion, dated Jan. 26, 2018, for PCT International Application Serial No. PCT/US17/62089 filed on Nov. 16, 2017.
International Search Report and Written Opinion, dated Jan. 30, 2019, for PCT International Application Serial No. PCT/US18/61550 filed on Nov. 16, 2018.
Kilsdonk et al., Cellular cholesterol efflux mediated by cyclodextrins. Journal of Biological Chemistry, American Society for Biochemistry and Molecular Biology, vol. 270, No. 29, pp. 17250-17256 (1995).
Lalefar et al., Wnt3a nanodisks to promote ex vivo expansion of hematopoietic stem and progenitor cells. Journal of Nanobiotechnology, vol. 14, No. 66, pp. 1-10 (2016).
Supplementary European Search Report for Application No. 17870876 (search completed on Apr. 24, 2020).
Supplementary European Search Report for Application No. 18879769 (search completed on Apr. 7, 2021).
Szejtli, The properties and potential uses of cyclodextrin derivatives. Journal of Inclusion Phenomena and Molecular Recognition in Chemistry, vol. 14, No. 1, pp. 25-36 (1992).
Willert et al., Wnt proteins are lipid-modified and can act as stem cell growth factors. Nature, vol. 423, No. 6938, pp. 448-452 (2003).
Willert et al., Wnt proteins are lipid-modified and can act as stem cell growth factors. Supplement Material, Nature, vol. 423, No. 6938, pp. S1-S3 (2003).
Witkowski et al., Isolation and characterization of recombinant murine Wnt3a. NIH Public Access Author Manuscript (Protein Expression and Purification), vol. 106, pp. 41-48 (2015).
Yoshinori et al., Roles of the Hedgehog signaling pathway in epidermal and hair follicle development, homeostasis, and cancer. Journal of Developmental Biology, vol. 5, No. 12; 19 pages (2017).
Zidovetzki et al., Use of cyclodextrins to manipulate plasma membrane cholesterol content: Evidence, misconceptions and control strategies. Biochimica et Biophysica Acta, vol. 1768, No. 6, pp. 1311-1324 (2007).
Manicassamy et al., Activation of beta-catenin in dendritic cells regulates immunity versus tolerance in the intestine. Science, vol. 329, pp. 849-853 (2010).
Mikels et al., Wnts as ligands: processing, secretion and reception. Oncogene, vol. 25, pp. 7461-7468 (2006).
Anton Parr. Viscosity and pH in One Step—Quaioty Parameters for Nasal Sprays, available online at chrome-extension://efaidnbmnnnibpcajpcglclefindmkaj/https://www.hpcimedia.com/images/PDF/Viscosity_and_pH_of_Nasal_Sprays.pdf. 3 pages (first available 2015).
Bielefeld et al.: Cutaneous wound healing: recruiting developmental pathways for regeneration. Cell. Mol. Life Sci. 70:2059-2081 (2013).
Chinese Application No. 2017800835120 First Office Action dated Mar. 30, 2022.
Chinese Application No. 2018800741594 Second Office Action dated May 9, 2022.
EP21207848.9 European Search Report completed Feb. 16, 2022.
Glycerin Uses (C3H8O3)—Properties, Structure of Glycerin with FAQs & Videos. Available online at https://byjus.com/chemistry/glycerin/. 14 pages (accessed Oct. 18, 2022).
Japanese Application No. 2020-527102 Office Action dated Oct. 27, 2022.
Lawal et al.: Kosmotropes and chaotropes as they affect functionality of a protein isolate. Food Chem. 95:101-107 (2006).
Matencio et al.: Cyclic Oligosaccharides as Active Drugs, an Updated Review. Pharmaceuticals. 13:1-20 (2020).
Ng et al.: The Secreted Signaling Protein Wnt3 Is Associated with Membrane Domains In Vivo: A SPIM-FCS Study. Biophys. J. 111:418-429 (2016).

(56) References Cited

OTHER PUBLICATIONS

Portilho et al.: A soluble and active form of WNT-3A protein is involved in myogenic differentiation after cholesterol depletion. FEBS Letters 581:5787-5795 (2007).
Rushan et al.: Roles of the Wnt/β-catenin signaling pathway in hair follicle formation and hair growth. Int J Dermatol Venereol. 41(6):399-401 (2015).
Swelstad et al.: Current protocols in the generation of pluripotent stem cells: theoretical, methodological and clinical considerations. Stem Cells and Cloning. Adv. Appl. 3:13-27 (2010).
UFNAL et al.: TMAO: A small molecule of great expectations. Nutrition. 31 (11-12):1317-23 (2015).
U.S. Appl. No. 16/461,752 Final Office Action dated Dec. 17, 2021.
U.S. Appl. No. 16/461,752 Office Action dated Jun. 8, 2021.
U.S. Appl. No. 16/461,752 Office Action dated Sep. 21, 2022.
U.S. Appl. No. 16/763,963 Non-Final Office Action dated Oct. 25, 2022.
U.S. Appl. No. 16/763,963 Restriction Requirement dated Feb. 4, 2022.
U.S. Appl. No. 16/461,752 Restriction Requirement dated Mar. 2, 2021.
Witkowski et al.: Isolation and characterization of recombinant murine Wnt3a. Protein Expression and Purification. 106:41-48 (2015).
Zhao et al.: Wnt3a, a Protein Secreted by Mesenchymal Stem Cells Is Neuroprotective and Promotes Neurocognitive Recovery Following Traumatic Brain Injury. Stem Cells, pp. 1263-1272 (2016).
Chinese Patent Application No. 2018800741819 First Office Action dated Feb. 18, 2023.

\* cited by examiner

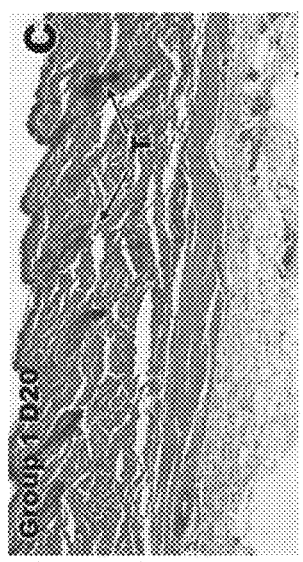
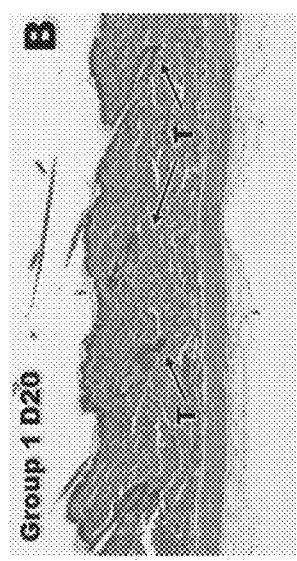
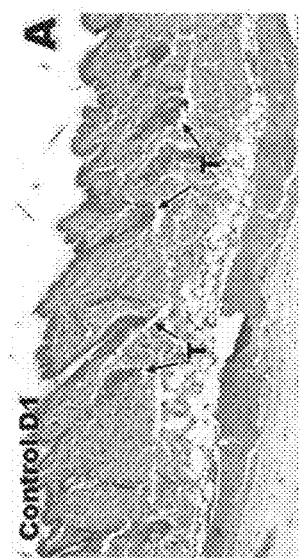
Figure 8A
Figure 8B
Figure 8C
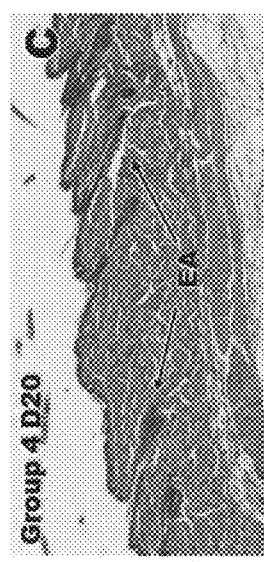
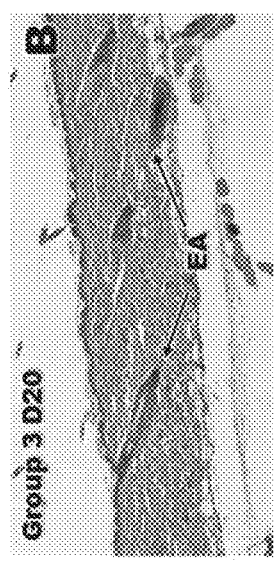
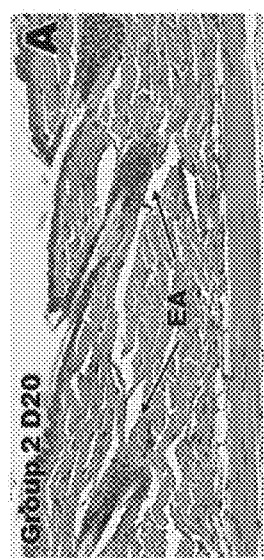
Figure 9A
Figure 9B
Figure 9C

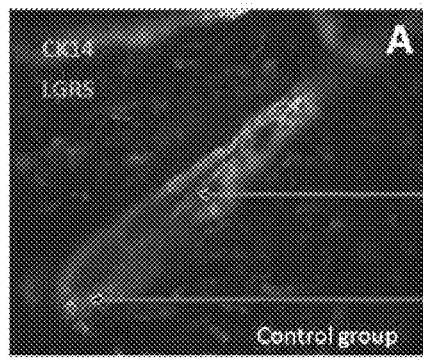 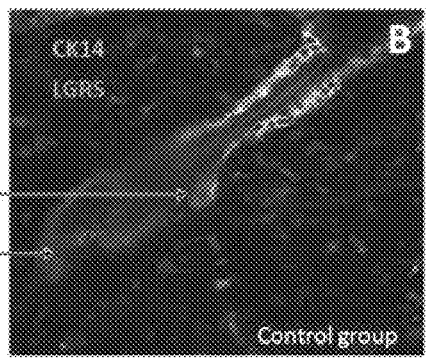
Figure 11A  Figure 11B
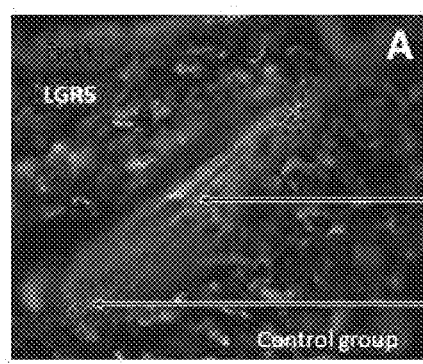 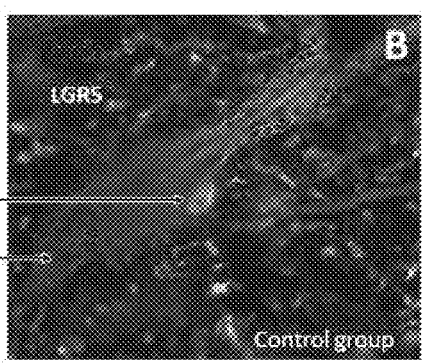
Figure 11C  Figure 11D
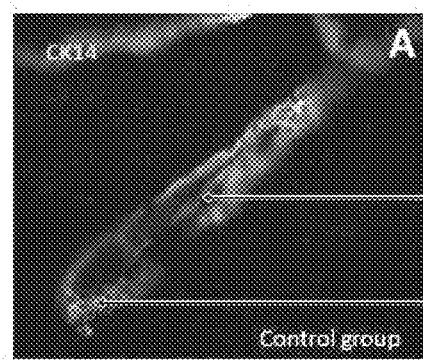 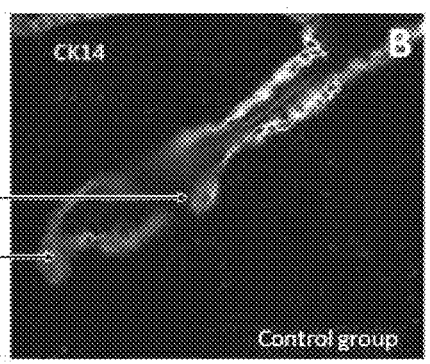
Figure 11E  Figure 11F

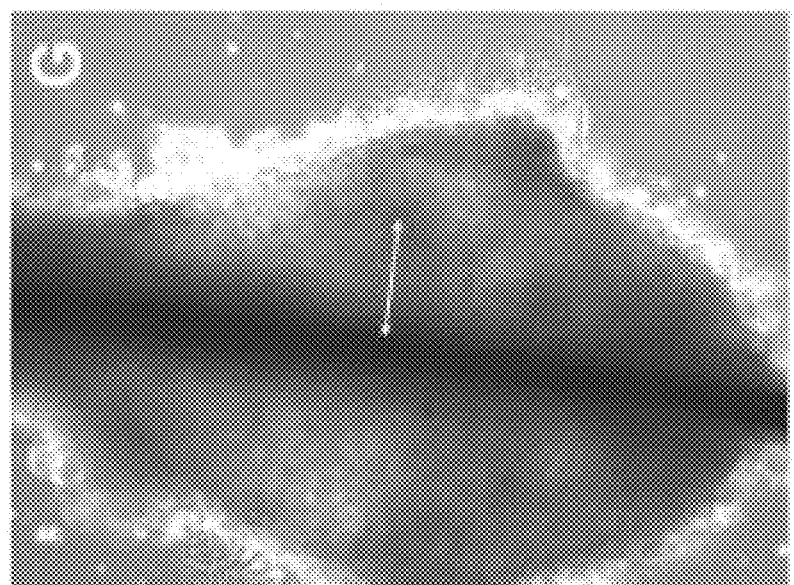
Figure 14D
Figure 14E
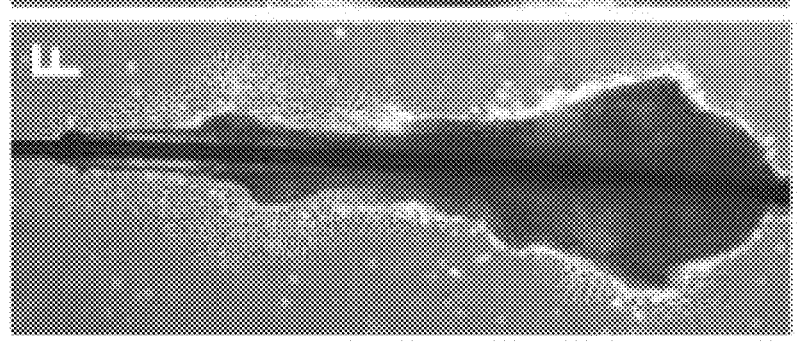
Figure 14F
Figure 14G
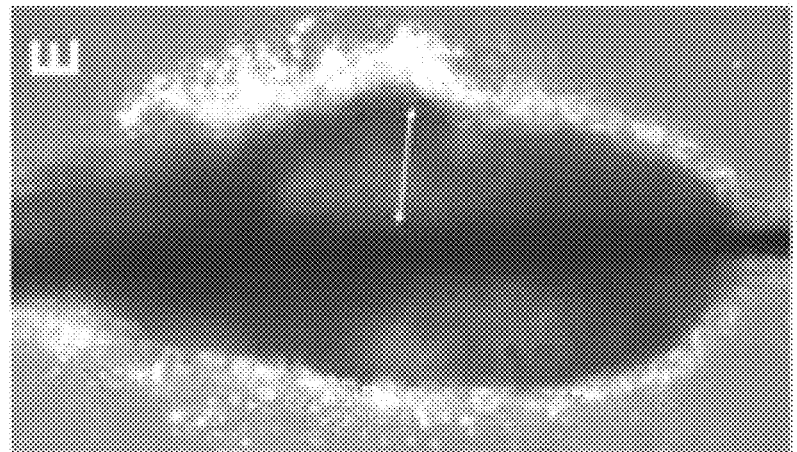
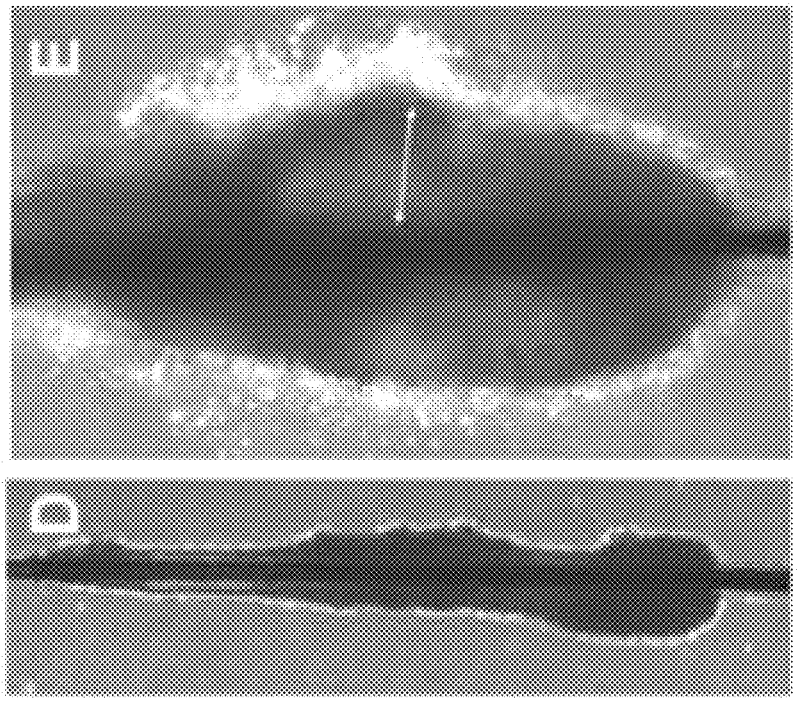
5 days MBCD exposure

USE OF CELL MEMBRANE-BOUND SIGNALING FACTORS

CROSS-REFERENCE TO RELATED APPLICATIONS

This application is a 35 U.S.C. 371 national phase entry of PCT/US2018/061550, filed Nov. 16, 2018, which claims the benefit of U.S. provisional patent application 62/587,338, filed Nov. 16, 2017; the entire contents of each of these applications are incorporated by reference herein.

BACKGROUND

Membrane bound signaling factors, including proteins of the Wingless (Wnt) and Hedgehog (Hh) families have the potential for use in a variety of disorders, however current methods of obtaining these proteins do not yield stable, efficacious molecules.

SUMMARY

Disclosed herein are compositions comprising a complex of lipid-modified proteins and a cyclodextrin as disclosed herein.

Also disclosed herein are injectable and topical compositions comprising the complex of lipid-modified proteins and a cyclodextrin as disclosed herein.

In some embodiments, the cyclodextrin is one or more of α-cyclodextrin, β-cyclodextrin, or γ-cyclodextrin. In some embodiments, the cyclodextrin is a chemically modified cyclodextrin, modified by hydrogenation, hydroformylation, methylation, oxidation, reduction, or a carbon-carbon coupling reaction. In some embodiments, the cyclodextrin is methyl-β-cyclodextrin or hydroxypropyl-beta-cyclodextrin.

In some embodiments, the lipid-modified proteins comprise one or more Wingless (Wnt) or Hedgehog (Hh) proteins associated with a cell membrane lipid. In some embodiments, the Hh protein is one or more of a Sonic Hedgehog (SHh) protein, a Desert Hedgehog (DHh) protein, or an Indian Hedgehog (IHh) protein. In some embodiments, the Wnt protein is one or more of Wnt3a, Wnt7b, or Wnt10b. In some embodiments, the lipid-modified proteins comprise other proteins in addition to those belonging to the Wingless (Wnt) or Hedgehog (Hh) families.

In some embodiments, the lipid-modified proteins are harvested from a population of animal stem cells. In some embodiments, the stem cells are embryonic stem cells, parthenogenic stem cells, adult stem cells, fetal stem cells, or induced pluripotent stem cells. In some embodiments the stem cells are lineage committed multipotent stem cells. In some embodiments the lipid-modified proteins are harvested from a population of proliferating cells. In some embodiments, the stem cells are mammalian cells. In some embodiments, the stem cells are human stem cells. In some embodiments the stem cells are from a domestic animal, for example a dog, a cat, a rabbit, a horse, a pig, or a bird. In some embodiments the stem cells are from an agricultural animal, for example, a cow, a sheep, a goat, a horse, a pig, a fish, a chicken, a duck, a goose, or a turkey. In some embodiments the stem cells are from a laboratory animal, for example, a mouse, a rat, a hamster, a guinea pig, a pig, a rabbit, a monkey, a bird, a chicken, a reptile, an amphibian, a frog, or a fish. The characterization of animals as laboratory, domestic or agricultural animals should not be considered as necessarily limiting, as the listed example are not exhaustive and some animals may reasonably fall within more than one category. In some embodiments, the stem cells are genetically engineered to overexpress Wnt or Hh proteins. The temporary or stable overexpression of Wnt and Hh ligands can be accomplished for example by introducing multiple copies of the respective genes, introducing translatable mRNA or by suppressing the regulatory genes. The methods include microinjection, the use of viral and retroviral vectors, electroporation, using plasmids, transposons or by targeted mutations using CRISPR-CAS9 system. In some embodiments ligands for receptor tyrosine kinases (RTK) are added to activate and increase Wnt or Hh expression. Such RTK include but not limited to epidermal growth factor (EGF), Insulin, platelet derived growth factor (PDGF), vascular endothelial growth factor (VEGF), FGF (fibroblast growth factor), NGF (nerve growth factor), receptor families. In some embodiments, the stem cells are genetically engineered to be immortal. In some embodiments, the stem cells are genetically engineered to express telomerase reverse transcriptase (hTERT)

In some embodiments, the composition further comprises at least one kosmotrope. In some embodiments, the at least one kosmotrope is propylene glycol, proline, trehalose, ectoine, or trimethylamine N-oxide.

In some embodiments, the injectable composition is in an aqueous formulation. In some embodiments, the injectable composition further comprises at least one kosmotrope. In some embodiments, the at least one kosmotrope is trehalose.

Disclosed herein are methods of promoting skin tissue regeneration, comprising exposing skin tissue to a topical composition or injectable composition disclosed herein. In some embodiments, the tissue can include epidermis, dermis or skin appendages such as hair, nails, glands and sensory receptors Also disclosed herein are methods of promoting tissue regeneration in a tissue in need thereof, comprising exposing a tissue to a composition disclosed herein. In some embodiments, the tissue is brain, heart, liver, spinal cord, bone, nervous tissue, reproductive organs, or any tissues other than skin or hair.

Also disclosed herein are methods of treating a neurodegenerative disorder comprising administration of a composition disclosed herein to a subject in need thereof. In some embodiments, the neurodegenerative disorder is Alzheimer's disease, Parkinson's disease, spinal cord injury, brain injury, peripheral nerve injury, peripheral neuropathy, multiple sclerosis, amyotrophic lateral sclerosis, or dementia.

As used herein, the term "treating" (and related forms of the word) does not necessarily mean curing in the sense restoring the affected individual to an undiseased state or completely and permanently resolving the underlying pathology. Rather in various embodiments the term "treating" can comprise slowing or halting the progression of disease, partial reversal of disease-related deficits or injuries, or amelioration or elimination of disease-associated symptoms. Similarly, the term "promoting regeneration" does not necessarily mean the complete restoration of the affected tissue, but in various embodiments can mean causing enough regenerative activity to slow or halt the loss of the affected tissue, or a partial restoration of the affected tissue.

Also disclosed herein are methods of producing a composition or topical composition disclosed herein comprising: culturing in a culture media stem cells which are capable of producing Wnt and Hh proteins; incubating the cells in a harvest solution comprising a cyclodextrin to obtain cyclodextrin complexes of lipid-modified proteins; preserving the cyclodextrin/lipid-modified protein complex solution; and mixing the preserved cyclodextrin/lipid-modified protein complex solution or the lyophilized cyclodextrin/lipid-modified protein complex with one or more cosmetic or pharmaceutically acceptable excipients.

In some embodiments, the harvest solution further comprises at least one kosmotrope. In some embodiments, the kosmotrope is trehalose. In some embodiments, the concentration of kosmotrope in the harvest solution is about 5% to about 30%. In some embodiments, the concentration of kosmotrope is 20%.

In some embodiments, the preserving step comprises storing the cyclodextrin/lipid-modified protein complexes solution at 4° C. or lower. In some embodiments, the preserving step comprises lyophilizing the cyclodextrin/lipid-modified protein complexes solution. In some embodiments, the preserved cyclodextrin/lipid-modified protein complexes are combined with one or more excipients to produce a topical formulation.

In some embodiments, the harvest solution comprises an aqueous solution of a cyclodextrin. In some embodiments, the cyclodextrin is methyl-β-cyclodextrin or hydroxypropyl-beta-cyclodextrin. In some embodiments, the concentration of cyclodextrin in the harvest solution is about 1 mM to about 20 mM. In some embodiments, the concentration of cyclodextrin in the harvest solution is about 10 mM.

BRIEF DESCRIPTION OF THE DRAWINGS

FIG. 4A depicts a portion of membrane with lipid-modified proteins and empty cyclodextrins. FIG. 4B depicts the lipid modification of the protein captured in the cyclodextrin hydrophobic core. The protein portion of the complex can be further stabilized with the addition of a kosmotrope that displaces water surrounding the protein molecule and preventing reactivity with other molecules.

FIG. 5A depicts cell cultures before exposure to the cyclodextrin-containing harvest solution which were smooth compact and multilayered. FIG. 5B depicts cultures after incubation with cyclodextrin wherein the cultures were disrupted with a majority of the cells losing adherence.

FIG. 7A depicts that treated animals displayed a hair growth response, regardless of the active concentration group. FIG. 7B depicts that treated animals displayed increased number of new anagen hair patches. FIG. 7C depicts that the response to treatment was confirmed by increased darkness of the skin in the treatment groups.

FIGS. 8A-C depict telogen status of hair follicles in treated mice. A sample was obtained at day one (D1) of the study to confirm that the mice are in the first telogen phase. The mice in the control group (Group 1, FIG. 8A) maintained the telogen (T) status of the hair follicles at the end of the study (D20) (FIGS. 8B and C).

FIGS. 9A-C depict telogen status of hair follicles in treated mice. The mice in the treatment groups (Groups 2, 3 and 4; FIGS. 9A, 9B, and 9C, respectively) displayed a mix of telogen and early anagen (EA) follicles in the area that was not containing new anagen patches.

FIGS. 10A, 10B, and 100, respectively) displayed patches of new anagen with typical anagen hair follicle morphology.

FIGS. 11A-F depict hair growth in two untreated mice. Two follicles (A and B) were stained for green expression of CK14 and red expression of LGR5. FIGS. 11A and 11B are composite images displayed in grayscale. Color separations of these images are displayed in grayscale shown in FIGS. 11C and 11D red fluorescence (LRG5) and FIGS. 11E and 11F green fluorescence (CK14) for follicles A and B, respectively. In control animals, the telogen stage persists with minimal or no Wnt activation, evidenced by very few LRG5 positive cells.

FIGS. 12A, 12D, and 12G depict treatment group 2 and is a photomicrograph of a new follicle. FIG. 12A being a grayscale image of the composite of the red (LGR5; FIG. 12D) and green (CK14; FIG. 12G) fluorescence. Expanding LGR5 positive bulge cells (B) migrating downwards and populating the new bulb matrix (MX). FIGS. 12B, 12E, and 12H depict treatment group 3 and is a photomicrograph of a new anagen follicle. FIG. 12B being a grayscale image of the composite of the red (LGR5; FIG. 12E) and green (CK14; FIG. 12H) fluorescence. Expanding LGR5 positive cells migrating downwards and populating the early anagen bulb (EA) next to a follicle in telogen (T). FIGS. 12C, 12F, and 12I depict treatment group 4 and is a photomicrograph of new anagen follicle. FIG. 12C being a grayscale image of the composite of the red (LGR5; FIG. 12F) and green (CK14; FIG. 12I) fluorescence. New follicle (EA) is below an old telogen follicle (T). LGR5 positive cells expanding the bulge area (B) and populating downwards the new bulb matrix (MX).

FIG. 13A depicts early anagen phase and FIG. 13B depicts anagen phase.

FIGS. 14A-G depict the effects of methyl-3-cyclodextrin (MBCD) on the in vitro growth of hair follicles in the absence of other growth factors at various concentrations after 2 days (FIGS. 14A-C) and 5 days (FIGS. 14D-G) of culture.

FIG. 15B depicts hair follicles displaying a statistical significant enhanced growth in thickness ($p<0.01$ for 0.25 mM and $p<0.05$ for the 0.5 mM group) grown in 0.25 mM and 0.5 mM MBCD complex.

FIGS. 16A and 16C depict an untreated area. FIGS. 16B and 16D depict a treated contralateral area with visible restored velus hair, longer velus hair, and reduced aging spots.

FIG. 18A is a grayscale image of the red channel of the color photograph of the treated culture representing the positive staining for Beta-III tubulin; FIG. 18B is a grayscale image of the blue channel representing the nuclear stain of the treated culture. FIG. 18C is a grayscale image of the red channel of the color photograph of the control culture representing the positive staining for Beta-III tubulin; FIG. 18D is a grayscale image of the blue channel representing the nuclear stain of the control culture.

FIG. 19A is a grayscale image of the red channel of the color photograph of the treated culture representing the positive staining for doublecortin; FIG. 19B is a grayscale image of the blue channel representing the nuclear stain of the treated culture. FIG. 19C is a grayscale image of the red channel of the color photograph of the control culture representing the positive staining for doublecortin; FIG. 19D is a grayscale image the blue channel representing the nuclear stain of the control culture.

DETAILED DESCRIPTION

Figure 1:
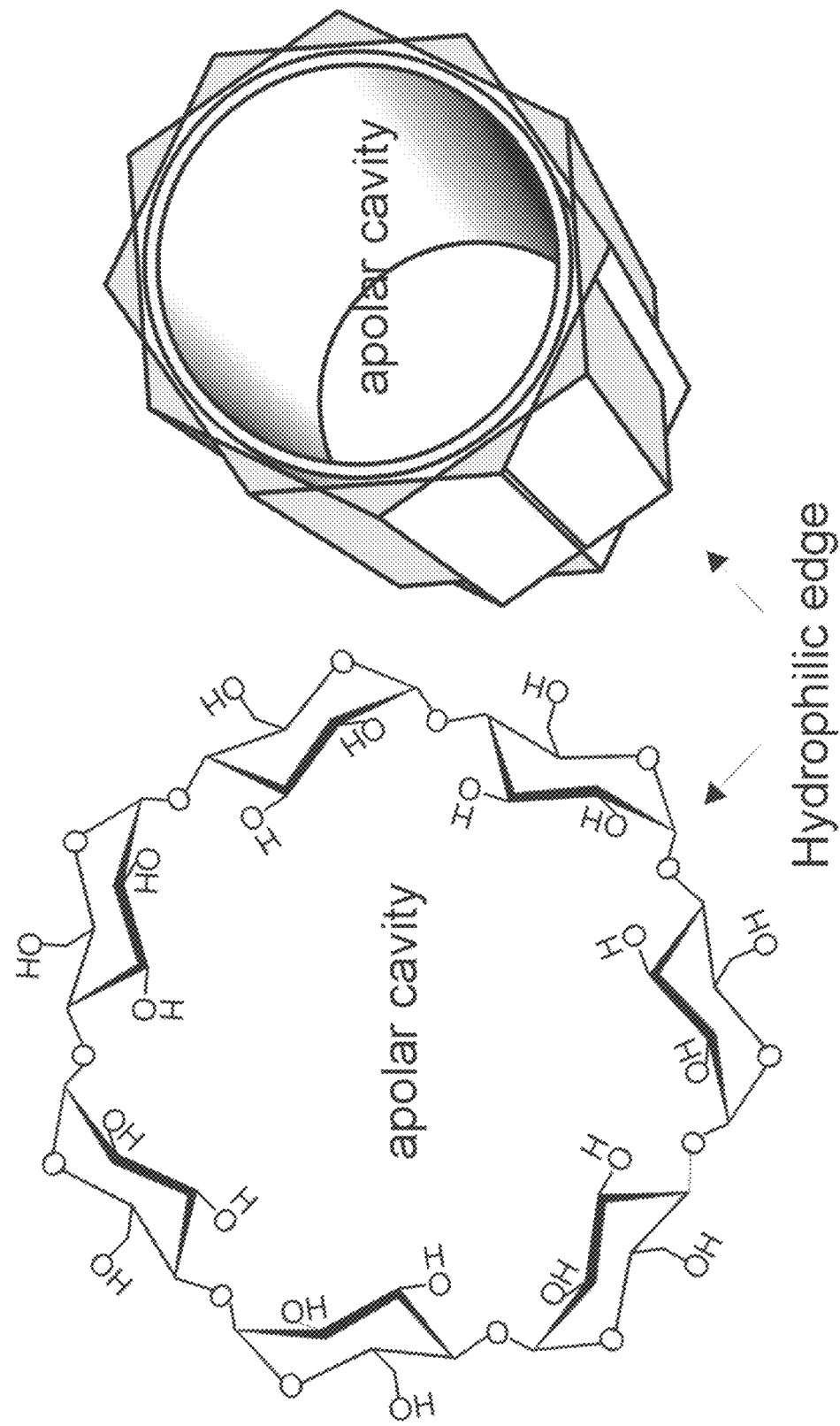
FIG. 1 depicts the chemical and physical structure of cyclodextrins.

Although Wingless (Wnt) and Hedgehog (Hh) proteins have been isolated and characterized, there is a very limited application of these factors. The sources of these proteins commonly are cells engineered to overexpress one single particular protein which is removed from the cell surface with mild detergents.

Disclosed herein are complexes of lipid-modified proteins from live cells and cyclodextrins. As used herein, the term "lipid-modified" refers to proteins having lipids covalently attached thereto. These lipid modifications arise from the normal biosynthetic processes of the live cells. Regarding Wnt and Hh, the proteins are modified with the fatty acid palmitate, although modification with other lipids, including cholesterol, is within the scope of the presently disclosed compositions and methods. Additional lipid modifications are presented in Table 1, below.

Stem cells that represent a transitional state from pluripotency to terminal differentiated stages express significant quantities of Wnt and Hh proteins. However, although the culture supernatants contain numerous soluble growth factors, Wnt and Hh proteins are not identifiable in the cell culture supernatant. Physiologic expression of Wnt and Hh leads to modification with lipids, causing them to become associated with the surface membrane of the expressing cell, rather than their secretion into the extracellular fluid. By exposing stem cells to a cyclodextrin solution, it is possible to successfully extract the lipid-modified Wnt and Hh proteins bound to the cholesterol-containing cell membrane, thus forming a soluble complex of the lipid-modified protein bound to the cyclodextrin. Adding trehalose to the soluble lipid-modified protein/cyclodextrin complex leads to the stabilization of the complex, allowing long-term storage of a lyophilized complex.

The Wnt and Hh proteins are effective in vitro and in vivo for promoting cell survival, proliferation, hair growth and tissue regeneration. The use of heterogeneous Wnt (e.g., Wnt3a, Wnt 7b, Wnt 10b, etc) and Hh mixtures obtained from characterized normal stem cell cultures is advantageous over the use of single factors obtained from modified cells engineered to express a particular protein as the combination of a variety of factors is required for proper stem cell function and therapeutic efficacy.

Thus, disclosed herein are methods for the capture of membrane-bound lipid-modified proteins from stem cells including embryonic stem cells, induced pluripotent stem cells, and adult stem cells. Examples of lipid-modified protein structures include, but are not limited to, proteins (ligands) in the Wnt and the Hh families. The cells are manipulated to maximize the expression of such proteins, then are exposed to cyclodextrins that are known for their ability to capture hydrophobic molecules. In some embodiments the lipid-modified protein expression profile of the manipulated cells is characterized. The cyclodextrin complexes are further coated with trehalose to confer protection from desiccation and protein denaturation.

Prior to the present disclosure, these lipid-modified proteins were extracted from cells with organic solvents or detergents. These methods have the disadvantage of conferring limited stability and functionality upon the extracted proteins. Organic solvents may denature the protein component and remove the lipid modification that is essential for the protein activity. Detergent extraction results in lipoprotein micelles that can be further included in liposomes. Although the detergent extraction method is superior to solvent extraction, the micelles and liposomes are unstable structures with limited shelf life.

The methods described herein ensure the capture of the lipid-modified proteins and allow the possibility of long-term preservation by lyophilization (freeze drying). The cyclodextrin/lipid-modified protein complexes are further preserved using trehalose, a kosmotropic agent that displaces the water surrounding proteins and lipids and ensures structure preservation.

The lipid-modified protein/cyclodextrin complexes isolated from stem cell cultures are useful in tissue repair, wound repair and regeneration, skin rejuvenation, hair growth, and cosmetics.

Cyclodextrins

There are three naturally occurring cyclodextrins, -α, -β, and -γ. The cyclodextrins form stable aqueous complexes with many other chemicals. Typical cyclodextrins comprise 6-8 glucopyranoside units, and can be topologically represented as toroids with the larger and the smaller openings of the toroid exposing to the solvent secondary and primary hydroxyl groups respectively. Because of this arrangement, the interior of the toroids is not hydrophobic, but considerably less hydrophilic than the aqueous environment and thus able to host other hydrophobic molecules. In contrast, the exterior is sufficiently hydrophilic to impart the cyclodextrins (or their complexes) with water solubility (FIG. 1).

The formation of the inclusion complexes greatly modifies the physical and chemical properties of the guest molecule, mostly in terms of water solubility, thus inclusion complexes of cyclodextrins with hydrophobic molecules are able to penetrate body tissues, and release the biologically active hydrophobic compounds under specific conditions including, but not limited to, pH change, heat, enzymes able to cleave α-1,4 linkages between glucose monomers, or displacement by other hydrophobic molecules (cholesterol for example).

Depending on the number of glucose rings in the molecule, the cyclodextrins are classified as α (alpha)-cyclodextrin (6-membered sugar ring molecule), β (beta)-cyclodextrin (7-membered sugar ring molecule), or γ (gamma)-cyclodextrin (8-membered sugar ring molecule). Because cyclodextrins are hydrophobic inside and hydrophilic outside, they can form complexes with hydrophobic compounds. Thus they can enhance the solubility and bioavailability of such compounds. This is of high interest for pharmaceutical as well as dietary supplement applications in which hydrophobic compounds are delivered. α-, β-, and γ-cyclodextrin are all generally recognized as safe by the FDA.

Chemical modifications of the naturally-occurring cyclodextrins can be engineered to increase the solubility, accommodate specific hydrophobic molecules, provide a termination that can be used for attachment to other molecules, provide a specific functionality, such as attachment to specific cell components, and self-assembly in macromolecular structures. Common modifications include random methylation and hydroxypropylation.

Both β-cyclodextrin and methyl-β-cyclodextrin (MBCD) remove cholesterol from cultured cells. The methylated form (MBCD) is more efficient than β-cyclodextrin at removing cholesterol from cultured cells. The water-soluble MBCD forms soluble inclusion complexes with cholesterol, thereby enhancing its solubility in aqueous solution. MBCD is employed for the preparation of cholesterol-free products; the bulky and hydrophobic cholesterol molecule is easily lodged inside cyclodextrin rings that are then removed. MBCD is also employed in research to disrupt lipid rafts by removing cholesterol from membranes.

Some embodiments specifically include one or some of the above disclosed cyclodextrins. Some embodiments specifically exclude one or some of the above disclosed cyclodextrins.

Kosmotropes

Kosmotropes cause water molecules to favorably interact, which also (in effect) stabilizes intramolecular interactions in macromolecules such as proteins. Exemplary kosmotropes include, but are not limited to, propylene glycol, proline, trehalose, ectoine, and trimethylamine N-oxide. Trehalose (mycose, tremalose) is a disaccharide comprised of two glucose molecules. Some embodiments specifically include one or some of the above disclosed kosmotropes. Some embodiments specifically exclude one or some of the above disclosed kosmotropes.

Trehalose's main biological purpose in mushrooms and bacteria is water regulation, since it forms a gel phase during cellular dehydration protecting organelles during this time and then allows rapid rehydration when a proper environment is reintroduced. It serves a hydration function in humans as well as possessing general antioxidant properties, but its major role is as a cellular chaperone regulating intracellular functions such as protein folding and unfolding.

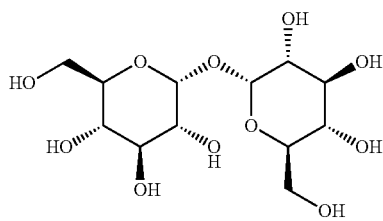

Chemical structure of trehalose

Trehalose has been classified as a kosmotrope or water-structure maker; that is the interaction between trehalose/water is much stronger than water/water interaction and may be involved in its bioprotective action.

Figure 2:
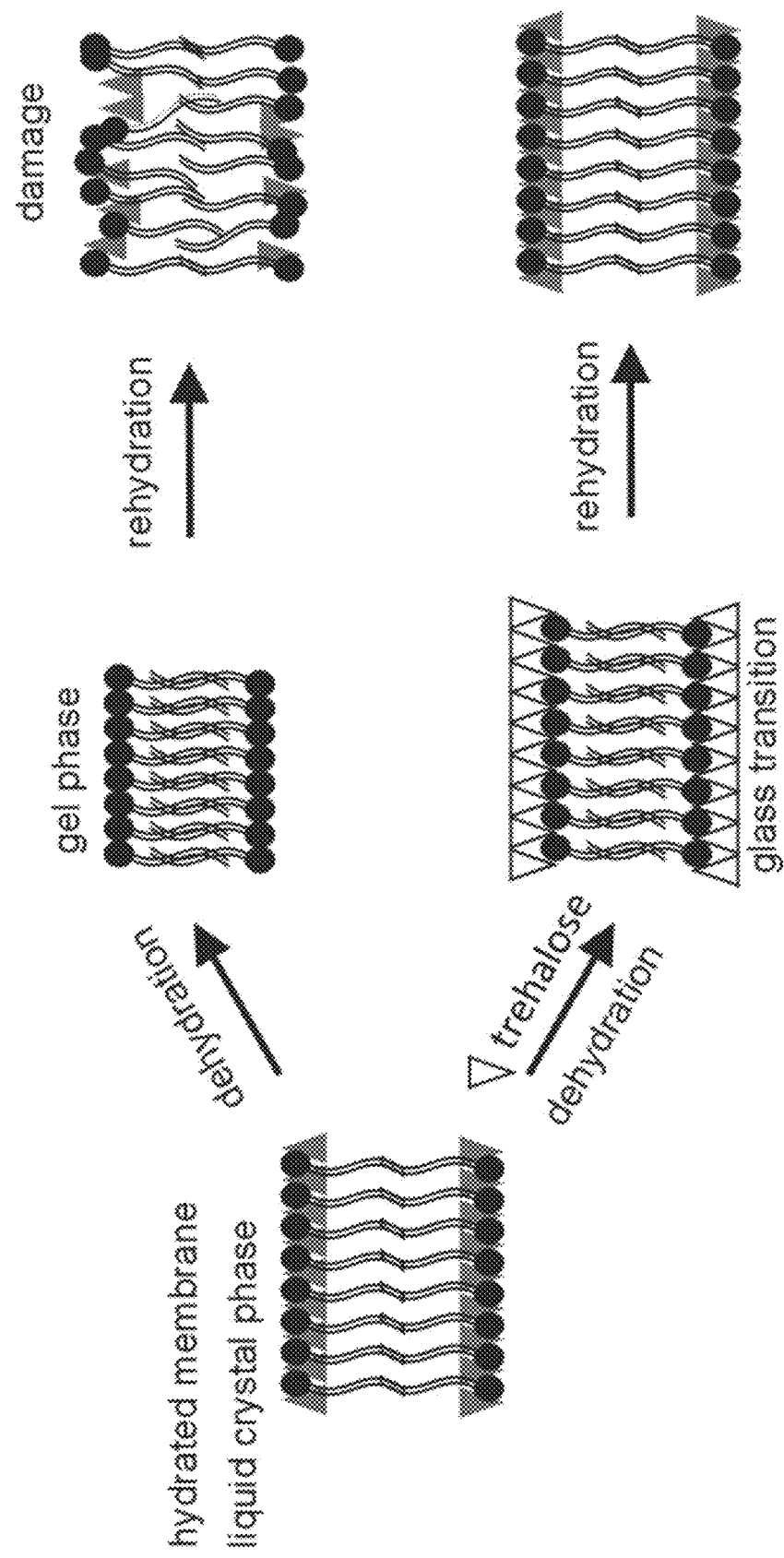
FIG. 2 depicts a schematic representation of the trehalose effect on stabilizing lipid membranes during dehydration.

Trehalose can inhibit protein aggregation, acting as a stabilizer to improve the shelf-life of therapeutic proteins. Work with model proteins has shown that trehalose is able to abrogate the moisture-induced aggregation of bovine serum albumin by interfering with the formation of intermolecular disulphide bonds. Trehalose is effective in stabilizing lipid membranes and protection against dehydration. The lipid bilayer would otherwise undergo a liquid crystal to gel transition during dehydration, permanently compromising the bilayer structure. Trehalose, by replacing the water, occupies the spaces between lipids and maintains the organized liquid crystal structure upon rehydration (FIG. 2).

Hedgehog (Hh) and Wingless (Wnt) Families

Mammals have three Hedgehog homologues, Desert (DHh), Indian (IHh), and Sonic (SHh) Hedgehog, of which Sonic is the best studied. The signaling pathways were studied in knockout mice and demonstrated cell specificity for brain, skeleton, musculature, gastrointestinal tract, lungs, and heart. Recent studies point to the role of Hedgehog signaling in regulating adult stem cells involved in maintenance and regeneration of adult tissues. The pathway has also been implicated in the development of some cancers. Drugs that specifically target Hedgehog signaling to fight cancer are being actively developed.

Attachment of lipophilic groups is a widespread modification that occurs on nearly 1,000 proteins of diverse structure and function (Table 1). At least five different types of lipids can be covalently attached to proteins including, but not limited to, fatty acids, isoprenoids, sterols, phospholipids, and glycosylphosphatidyl inositol (GPI) anchors. Proteins can contain more than one type of lipid, e.g. myristate+palmitate, palmitate+cholesterol, or farnesyl+palmitate. The most common outcome of lipid modification is an increased affinity for membranes

TABLE 1

| | | Representative lipid-modified proteins | |
|---|---|---|---|
| Lipid 1 | Lipid 2 | Protein | Localization |
| Myristate | | Protein kinase A, catalytic subunit | Cytosolic |
| | | MARCKS | Plasma membrane/cytoskeleton |
| | | ARF1 | Golgi<—>cytosol |
| | | c-Src | Plasma membrane/endosomes |
| | Palmitate | Src family kinases (SFKs) | Plasma membrane/endosomes |
| | | Gα subunits | Plasma membrane/cytosol |
| | | AKAPs | Plasma membrane/intracellular organelles |

TABLE 1-continued

Representative lipid-modified proteins

| Lipid 1 | Lipid 2 | Protein | Localization |
|---|---|---|---|
| Palmitate | | Transferrin Receptor | Plasma membrane |
| | | GPCRs | Plasma membrane |
| | | PSD95 | Postsynaptic density (PSD) |
| | Cholesterol | Hedgehogs (Sonic, Indian, Desert) | Secretory pathway, extracellular space |
| Palmitoleate | | Wnts | Secretory pathway, extracellular space |
| Oleate | | Ghrelin | Secretory pathway, extracellular space |
| Farnesyl | Palmitate | H-Ras, N-Ras | Plasma membrane, Golgi |
| Farnesyl | | K-Ras4B | Plasma membrane |
| | | LaminB | Nuclear envelope |
| Geranylgeranyl | | Rabs, Rhos | Plasma membrane, Golgi, intracellular vesicles |
| Phosphatidyl-ethanolamine | | Atg8/LC3 | Autophagosome |
| GPI anchor | | NCAM | Outer leaflet of plasma membrane |
| | | 5' Nucleotidase | Outer leaflet of plasma membrane |
| | | CD55 | Outer leaflet of plasma membrane |
| | | Thy1 | Outer leaflet of plasma membrane |

The Hh protein is made as a precursor molecule, comprising a C-terminal protease domain and an N-terminal signaling unit, and undergoes a number of unusual modifications during its synthesis. The N terminus of Hh becomes modified by the fatty acid palmitate, on a conserved cysteine residue that is exposed at the very N-terminal end of the protein after its signal sequence has been removed. The palmitoyl group is attached through an amide to the NH2 group of the cysteine, Wnt molecules are palmitoylated and are therefore much more hydrophobic than predicted from their primary amino acid sequences. The amino acid of Wnt proteins that appears to be modified is the first conserved cysteine (C77), a residue that is present in all Wnts and that is essential for Wnt function, as revealed by mutant analysis.

Because lipid modification which confers hydrophobicity, Hh and Wnt cannot be distributed systemically; the proteins are membrane-bound and can only be transmitted from cell to cell amongst cells that are in direct contact. In contrast, soluble factors (such as FGF, EGF etc) are distributed systemically and can exercise effects on regional or distant cells.

An originating cell (stem cell) expressing the Engrailed (En) transcription factor secretes Hh. Only cells adjacent to En-expressing cells are able to respond to Hedgehog following interaction of Hh with the receptor protein Patched (Ptc).

Figure 3:
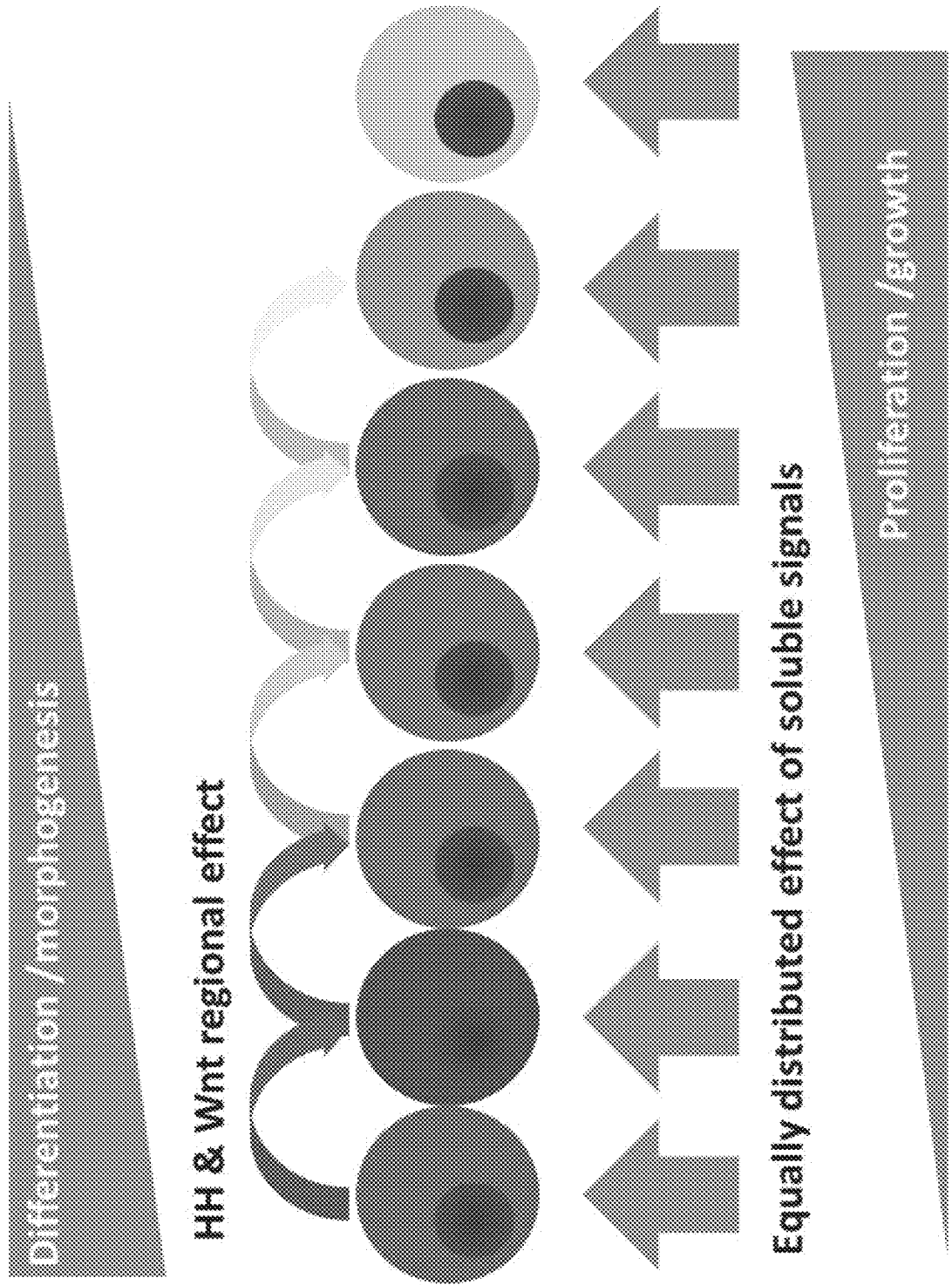
FIG. 3 depicts interactions between local and regional factors in morphogenesis and tissue growth.

Cells with Hh-activated Ptc synthesize the Wnt protein. The Wnt lipid-modified protein acts as an intercellular signal and patterns the adjacent rows of cells by activating its cell surface receptor Frizzled. Thus, the effects of Wnt and Hh on adjacent cells establishes a positional code that accounts for the distinct anatomical features, while the soluble factors establish a temporary code for cell proliferation and tissue growth (FIG. 3).

The hair follicle is a heterogenous structure, sometime termed a "mini-organ," formed with neuroectodermal-mesodermal interaction. Hair follicle neogenesis occurs in the embryo by invagination of the epidermal placode into the surrounding dermis. Postnatal follicles undergo a cycle of renewal in 3 phases: anagen (growth), catagen (regression), and telogen (resting). The first complete postnatal hair follicle cycle (first anagen, first catagen, first telogen) is completed in the first 3.5 weeks after birth and is followed by the second hair cycle (second anagen, second catagen, second telogen).

In skin, the formation of hair follicles from developing epidermis requires signals from fibroblasts in the underlying dermis. Hair follicle morphogenesis takes place during the late embryonic and early neonatal period. Adult skin does not normally give rise to new follicles.

Hair follicle neogenesis can be induced in adult mouse skin in response to transgenic or wound-induced epidermal activation of Wnt/β-catenin. Inhibition of Wnt signaling by DKK1 (Dickkopf-related protein 1) demonstrates the functional importance of Wnt signaling in hair follicle development. Several Wnt molecules are expressed in the hair follicle and could serve this function. Wnt3a and Wnt7a are expressed in the follicular matrix cells and maintain dermal papilla cells in the anagen phase. These cells are likely to be capable of responding to Wnt because they express components of the Wnt signal transduction cascade including frizzled7, disheveled2, GSK3β, β-catenin, and Lef1. Thus, the Wnt pathway is considered to be the master regulator during hair follicle morphogenesis. Wnt signaling proceeds through EDA/EDAR/NF-κB (ectodysplasin A/ectodysplasin A receptor/nuclear factor kappa-light-chain-enhancer of activated B cells) signaling. NF-κB regulates the Wnt pathway and acts as a signal mediator by upregulating the expression of SHh. Dermal SHh and platelet-derived growth factor (PDGF) signaling up-regulates dermal noggin expression; noggin is a potent inhibitor of bone morphogenic protein (BMP) signaling which helps in counteracting BMP-mediated β-catenin inhibition. This interplay of signaling between the epithelial and dermal lineage helps in epithelial SHh signal amplification.

The relevance of SHh to hair development has been suggested by the SHh expression pattern during embryogenesis and by manipulation of SHh expression throughout embryonic development. During normal hair follicle development, SHh is expressed in follicles in the epidermal placode, and its receptor Ptc is detected in underlying mesenchymal condensation at an early embryonic age.

In vivo experiments have suggested that SHh stimulates the transition from telogen to anagen possibly in collaboration with other local factors. Transient expression of SHh could re-activate the hair growth cycle in disease conditions.

In mammals, despite considerable ability for tissue regeneration, large wounds result in the formation of scar tissue instead of a complete restoration of tissue morphology and function. This limited regenerative capacity is partly due to rapid interposition of fibrotic tissue, something that prevents subsequent tissue regeneration, but might be a defensive advantage in preventing harmful microbes. If injured, only bone, liver, and infant finger tips can regenerate. Aging is another determinant for tissue restoration, as animals gradually lose their regenerative capacity as they get older.

Repaired skin, which usually heals as a scar, is weaker than intact skin, and contains a disorganized extracellular matrix (ECM) compared to non-wounded skin. Cutaneous wounds do not normally regenerate hair follicles. As a result, postnatal mammalian skin repair is not identical to the process of regeneration of early gestational fetal wounds in which the regenerated tissue is almost indistinguishable from the uninjured tissue.

Wnt proteins may participate in stimulating dermal β-catenin during wound repair, although Wnt signaling is not crucial for maintaining elevated β-catenin levels during the proliferative phase of cutaneous healing. Analogous to its function in skin development, Wnt and/or β-catenin signaling plays an important role in various aspects of cutaneous wound repair, involved in the construction of epithelial structures and in the reconstitution of the dermal compartment.

Wnt signaling regulates cell proliferation in the adult epidermis, which directly impacts the rate and extent of skin wound healing. Wnts also serve as niche signals for at least two types of skin stem cells, those in the bulge region of the hair follicle and those in the basal layer of the interfollicular epidermis, and these stem cells contribute to cutaneous wound repair. Topical application of liposomal Wnt3a to a non-healing wound supplements endogenous Wnt signaling, and results in better skin wound healing.

Wnt signaling is also important in the central nervous system. It has been suggested that the activation of the Wnt signaling pathway could be important in the regenerative response after CNS injury, activating diverse protective mechanisms including the stimulation of neurogenesis, blood brain structure consolidation and the recovery of cognitive brain functions.

Hedgehog signaling was shown to directly contribute for normal and accelerated wound healing in mice. When Hh signaling is inhibited, all aspects of wound healing (wound closure, epithelialization, granulation formation, vascularity, and proliferation) are severely impaired.

In the skin, touch domes develop in tandem with primary hair follicles and contain sensory Merkel cells. Dermal Wnt signaling, and subsequent epidermal Eda/Edar (ectodysplasin/ectodysplasin receptor) signaling, promote Merkel cell morphogenesis by inducing SHh expression in early follicles. Although developmentally associated with hair follicles, fate mapping demonstrated Merkel cells primarily originated outside the hair follicle lineage. These findings suggest that touch dome development requires Wnt-dependent mesenchymal signals to establish reciprocal signaling within the developing ectoderm SHh signaling from primary follicles to extrafollicular Merkel cell progenitors. Locally-produced SHh acting as a morphogen is essential for lineage specification during development and postnatal touch dome stem cell maintenance.

During development, SHh is required for lineage specification and proliferation of oligodendrocyte progenitors (OLPs), which are the glia cells responsible for the myelination of axons in the central nervous system (CNS). SHh signaling has been implicated in controlling both the generation of oligodendrocytes (OLGs) during embryonic development and their production in adulthood.

In amphibians, Hh signaling, and its hierarchical correlation with respect to Wnt signaling, controls limb regeneration. Wnt signaling has been shown to promote self-renewal in both gut epithelial and hematopoietic stem cells (HSCs). Stem cells in many tissues are responsive to Wnt (Table 2).

TABLE 2

Examples of Wnt-responsive tissue stem cells identified by means of lineage tracing.

| Tissue | Stem cell |
| --- | --- |
| Intestine | Crypt base columnar cell |
| Mammary gland | Basal cell |
| Stomach | Basal pyloric cell |
| Interfollicular epidermis | Basal cell |
| Central nervous system | Radial glial cell |
| Hair follicle | Outer bulge cell |
| Kidney | Nephron segment-specific stem cell |
| Cochlea | Tympanic border |
| Ovary | Hilum ovarian surface epithelial cell |
| Taste bud | Circumvallate papilla stem cell in posterior tongue |
| Brain | Neurogenesis area of hippocampus, subventricular zone |
| Retina | Retinal progenitor cells |

Along with the lipid-modified proteins bound to cell membranes, lipids are also involved in cell signaling including, but not limited to, sphingolipid based lipids (e.g., ceramide, sphingosine, sphingosine-1-phosphate, glucosylceramide, ceramide-1-phosphate, phosphatidylinositol bisphosphate ($PIP_2$) lipid agonist; phosphatidylinositol based lipids (e.g., phosphatidylinositol bisphosphate (PIP2)); activators of G-protein coupled receptors (e.g., lysophosphatidic acid (LPA), sphingosine-1-phosphate (S1P), platelet activating factor (PAF), endocannabinoids, prostaglandins, FAHFA, retinol derivatives); and activators of nuclear receptors (e.g., steroid hormones, retinoic acid, prostaglandins).

Compositions

Thus, disclosed herein are compositions comprising lipid-modified Hedgehog (Hh) and/or Wingless (Wnt) proteins and at least one cyclodextrin. The lipid-modified Hh and/or Wnt proteins are isolated from human stem cells as described herein. In certain embodiments, the stem cells are pluripotent, multipotent, single lineage dividing progenitors, or immortalized cell lines.

In certain embodiments, the source cells for the Wnt and Hh proteins are human embryonic, parthenogenic, or induced pluripotent stem cells. Other cells of interest include any in vitro proliferating cells that have been identified as fetal or adult stem cells, or sourced from fetal annexes. Other cells can be modified with a genetic manipulation that confers immortality by cell cycle deregulation, for example telomerase expression. In certain embodiments, the stem cells are immortalized by the genetically engineered expression of telomerase reverse transcriptase (hTERT). Source cells can be cultivated using established methods and cell culture media as known to persons of ordinary skill in the art. In some embodiments the stem cells are freshly obtained. In other embodiment the stem cells are expanded in-vitro by cell culture techniques prior to the lipid-modified proteins being harvested. In some embodiments the stem cells have been previously frozen. In some embodiments the previously-frozen stem cells are cultivated in vitro by passaging at least 1 time after being thawed prior to the lipid-modified proteins being harvested.

In some embodiments, the Hh or Wnt proteins are harvested by: first discarding the culture media, rinsing the cultures with an isotonic buffer (e.g. saline, Hanks, balanced salt solution etc), then combining cells with of a harvesting solution for about 1 hour to about 24 hours, optionally with slow, continuous, or intermittent agitation. Some of the cells may lose the attachment to substrate. The harvested solution, containing the soluble lipid-modified protein/cyclodextrin complexes is further processed to remove cell debris (example centrifugation and filtration through a 0.1-0.5 µm) filter and stored at 4° C.

Harvesting solutions suitable for obtaining lipid-modified Wnt and Hh proteins from stem cells comprise isotonic solutions containing about 1-20 mM of a cyclodextrin. In some embodiments, the concentration of cyclodextrin is about 1-5 mM, about 5-10 mM, about 10-15 mM, about 15-20 mM, about 2-10 mM, about 5-20 mM, about 8-20 mM, about 12-20 mM, about 8-12 mM, about 5 mM, about 7 mM, about 9 mM, about 10 mM, about 11 mM, about 13 mM, or about 15 mM. The volume of harvesting solution is about 0.1-1.0 mL/cm² of dish or flask. In some embodiments, the volume of harvesting solution is about 0.25 mL/cm² of dish or flask.

The harvesting solution is incubated with the source cells for about 1 hour to about 5 hours with slow, continuous, or intermittent agitation. In some embodiments, the harvesting solution is incubated with the cells for about 1 hour, about 1.5 hours, about 2 hours, about 2.5 hours, about 3 hours, about 3.5 hours, about 4 hours, about 4.5 hours, or about 5 hours.

In typical embodiments the lipid modified Wnt and Hh proteins are present in the harvest solution, post-harvest, at ng/ml concentrations (see for example, Tables 5 and 6 in the Examples, below). This is at least a 1000-fold enrichment over the amount of these proteins that would be present if there were no cyclodextrin in the harvest solution, if Wnt or Hh proteins were present in detectable quantities at all. In various embodiments the harvest solution has a concentration of about 1 to about 25 ng/ml, or of about any integer or integer-bound within that range, of a lipid modified Wnt or Hh protein. As pharmaceutical and cosmeceutical compositions may contain 0.1 to 100% harvest solution the lipid modified Wnt and Hh proteins can be present in these compositions in pg/ml and ng/ml concentrations, and at least exceeding 0.1 pg/ml. Thus in various embodiments pharmaceutical or cosmeceutical compositions comprise a concentration of a lipid modified Wnt and Hh protein of $1 \times 10^{-1}$ to 25 ng/ml or of any integer or integer-bound within that range. In some embodiments the lipid-modified is a Wnt protein or a Hh protein or a combination thereof. Is aspects of these embodiments the Wnt protein is Wnt3a, Wnt 7b, Wnt10b, or any combination thereof. In other aspects of these embodiments the Hh protein is SHh, DHh, IHh or any combination thereof.

The cells remain metabolically active during the harvest process and continue to secrete soluble proteins. Thus the harvest solution can contain these soluble proteins in addition to the cyclodextrin complexed lipid-modified proteins. Some embodiments specifically comprise these soluble proteins.

In some embodiments, the cyclodextrin is one or more of an α-cyclodextrin, a β-cyclodextrin, or a γ-cyclodextrin. In some embodiments, the, natural cyclodextrins are chemically modified by hydrogenation, hydroformylation, oxidation, reduction and carbon-carbon coupling reactions. Such well known modifications include 2-hydroxypropyl β-cyclodextrin and methyl-β-cyclodextrin. In some embodiments, the cyclodextrin is methyl-β-cyclodextrin (MBCD).

In certain embodiments, the harvest solution further comprises a kosmotrope. One exemplary method for harvest solution preparation includes the addition of a kosmotropic agent that displaces the water surrounding the protein molecule. An exemplary kosmotropic agent is trehalose that is added in the cyclodextrin complex solution for a final concentration between about 5% and about 30%. In other embodiments, the kosmotrope concentration is about 5% to about 10%, about 10% to about 15%, about 15% to about 20%, about 15% to about 25%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, or about 30%, or any concentration bounded by these values. In one embodiment, the trehalose concentration is 20% w/v added immediately after harvesting.

In some embodiments, the harvest solution comprises 10 mM cyclodextrin and 20% trehalose in water.

The cyclodextrin complex can be further preserved by lyophilization using a low temperature method (e.g., freeze-drying).

The detection of Wnt and Hh proteins in the disclosed compositions can be accomplished using a commercially available quantitative ELISA detection kits.

Figure 4A:
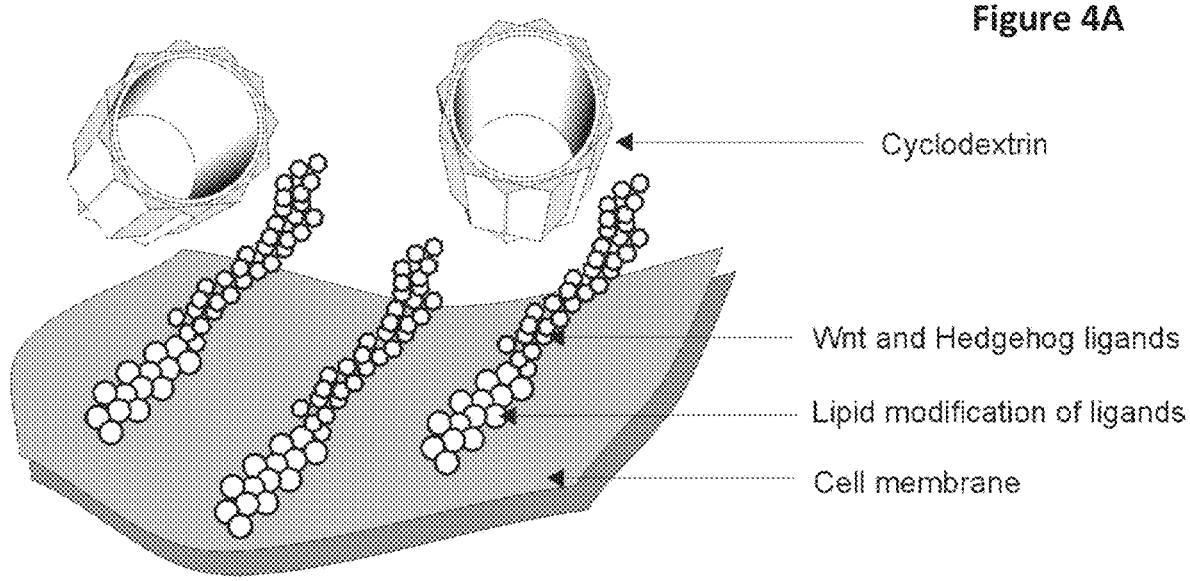
FIGS. 4A-B depict a schematic mechanism of membrane-bound lipid-modified protein capture using cyclodextrins.
Figure 4B:
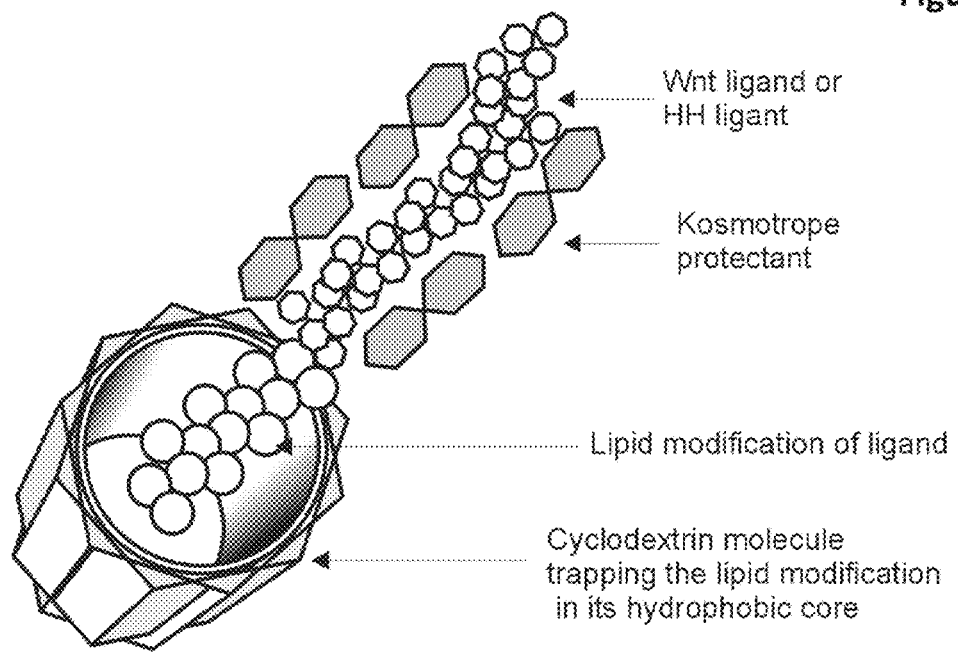
Figure 5A:
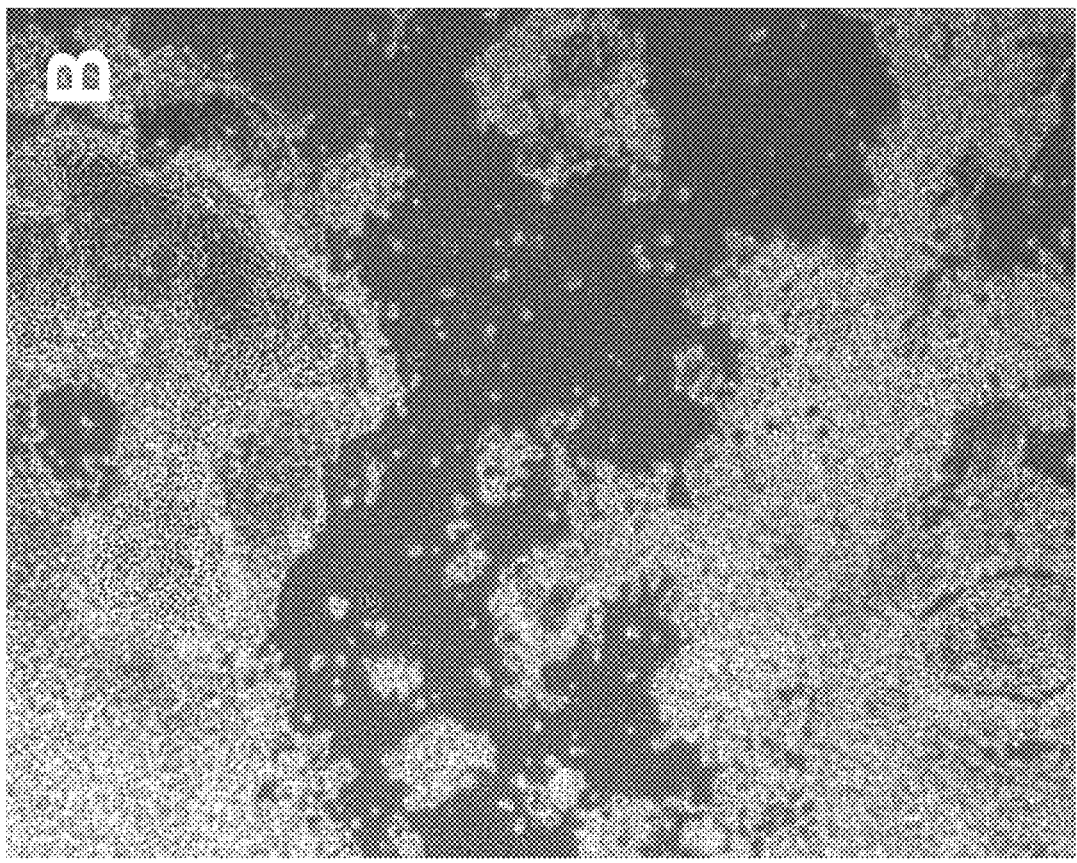
FIGS. 5A-B are phase contrast photomicrographs of cultured cells before and after harvest.
Figure 5B:
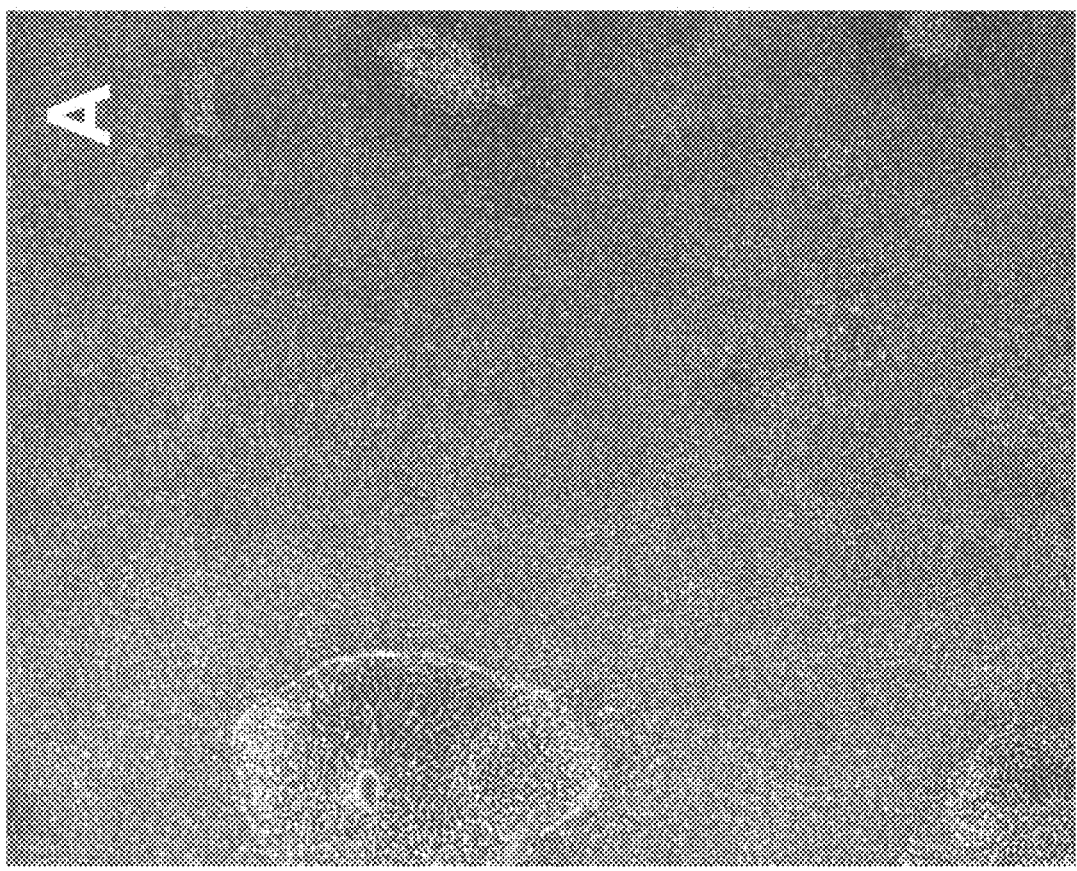
Figure 6B:
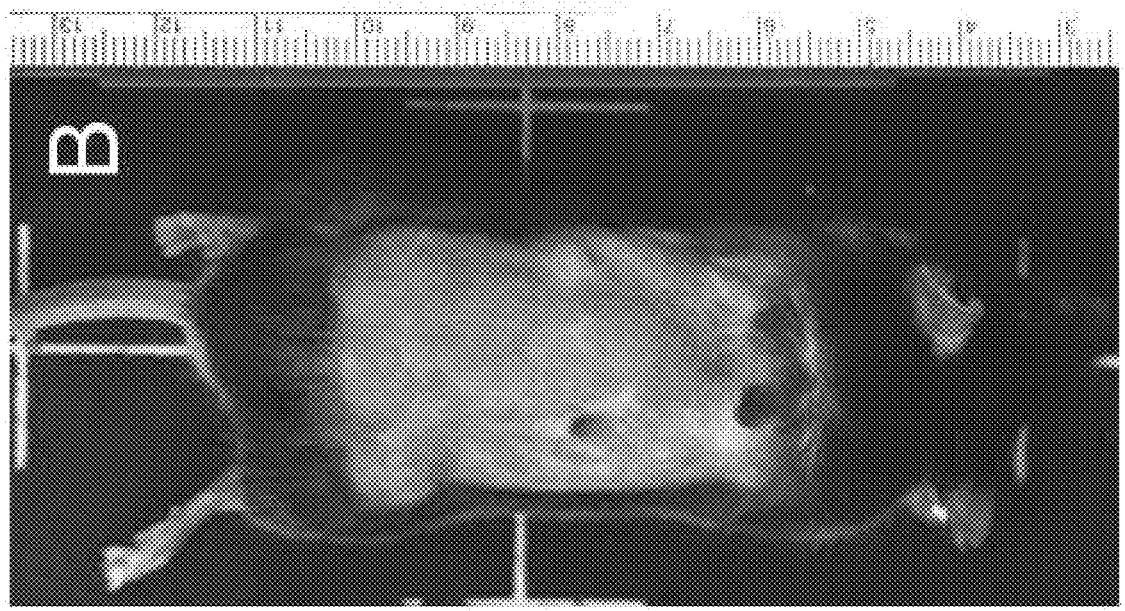
FIGS. 6A-D depict that mice in the treatment groups 1 (FIG. 6A), 2 (FIG. 6B), 3 (FIG. 6C), and 4 (FIG. 6D) demonstrated early transition to anagen by the presence of new anagen patches "anagen waves."
Figure 6A:
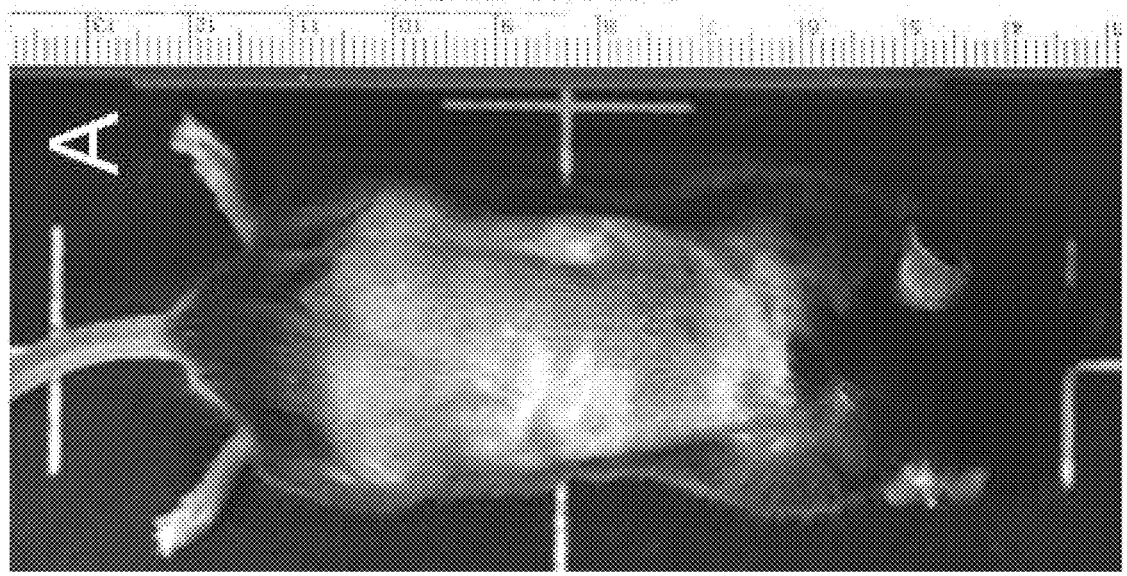
Figure 6D:
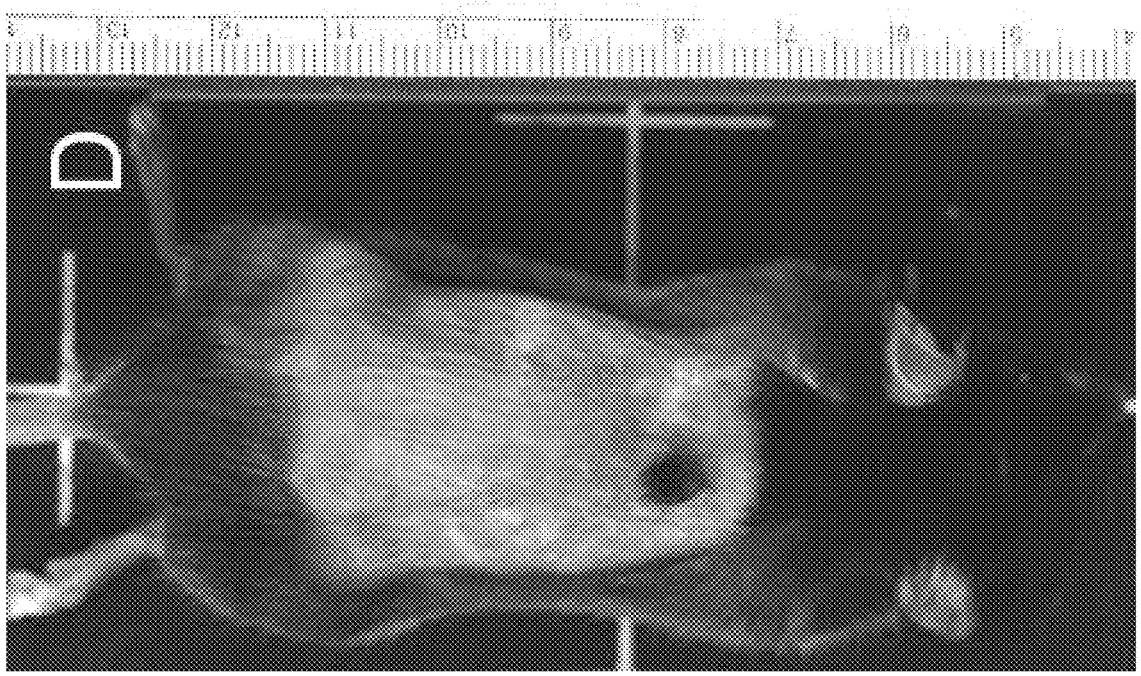
Figure 6C:
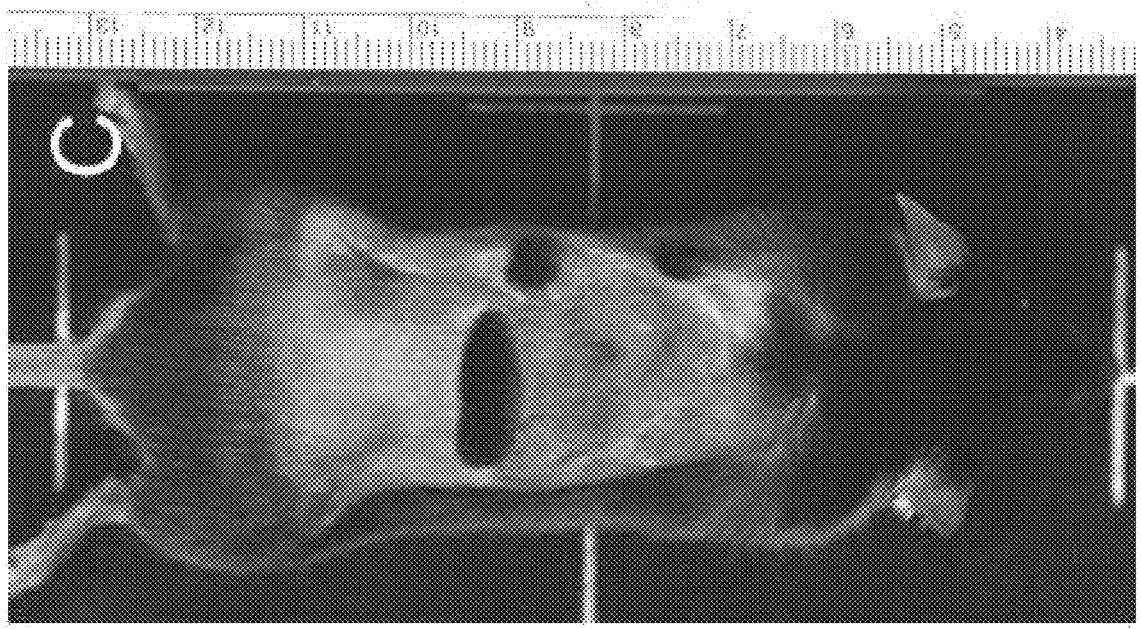

One embodiment of the lipid-modified protein/cyclodextrin complexes is disclosed herein is depicted in FIGS. 4A and 4B.

In one exemplary embodiment, a composition comprising Wnt/Hh-cyclodextrin complexes is an aqueous solution. The composition can further include one or more of amino acids, peptides, proteins, hydrosoluble vitamins and microelements. Exemplary components of the compositions include, but are not limited to hydro-soluble growth factors and steroid hormones and analogs thereof. Exemplary hydrosoluble growth factors include, but are not limited to, fibroblast growth factor (FGF), epidermal growth factor (EGF), keratinocyte growth factor (KGF), hepatocyte growth factor (HGF), etc.

According to some embodiments, a topical composition or formulation prepared according to the present disclosure may take the compositional form of a liquid, a paste, a cream, a lotion, a powder, an ointment, or a gel.

According to some embodiments, the compositional form is a paste, meaning a semisolid dosage form that contains one or more substances intended for topical application.

According to some embodiments, the compositional form is a cream. The term "cream" as used herein refers to a viscous liquid or semisolid emulsion of either the oil-in-water or water-in-oil type. As used herein "emulsion" refers to a colloid system in which both the dispersed phase and the dispersion medium are immiscible liquids where the dispersed liquid is distributed in small globules throughout the body of the dispersion medium liquid. A stable basic emulsion contains at least the two liquids and an emulsifying agent. Common types of emulsions are oil-in-water, where oil is the dispersed liquid and an aqueous solution, such as water, is the dispersion medium, and water-in-oil, where, conversely, an aqueous solution is the dispersed phase. It also is possible to prepare emulsions that are nonaqueous.

Creams of the oil-in-water type include hand creams and foundation creams. Water-in-oil creams include cold creams and emollient creams.

According to some embodiments, the compositional form is a lotion, meaning a liquid or semi-liquid preparation that contains one or more active ingredients in an appropriate vehicle. A lotion may be a suspension of solids in an aqueous medium, an emulsion, or a solution.

A "solution" generally is considered as a homogeneous mixture of two or more substances. It is frequently, though not necessarily, a liquid. In a solution, the molecules of the solute (or dissolved substance) are uniformly distributed among those of the solvent. Solvents that may be useful in the compositions of the present disclosure include water, as well as organic solvents, such as the alcohols.

According to some embodiments, the compositional form is an ointment. An ointment is a semi-solid preparation often intended for external application to the skin. Generally, ointment bases are categorized into hydrocarbon bases (oleaginous), adsorption bases (anhydrous); emulsion bases (water and oil type); and water soluble bases. Due to their anhydrous nature, ointments generally do not require any preservatives. They are more moisturizing and more occlusive than creams and form a protective film over the skin. The occlusive effect tends to prolong and enhance penetration.

According to some embodiments, the compositional form of the present disclosure is a gel. The term "gel" as used herein refers to a sticky, jelly-like semisolid or solid prepared from high molecular weight polymers in an aqueous or alcoholic base.

Additional compositional forms may be prepared using technology readily known in the formulation arts, such as those described in Remington: The Science and Practice of Pharmacy, 20th Ed. (Gennaro, A. R. et al., eds) Lippincott Williams & Wilkins: Philadelphia (2000), which is incorporated herein by reference.

A number of additional ingredients can be added to the compositions disclosed herein for functional, esthetic, and marketing purposes, including emulsifying agents, preservatives, humectants, thickeners, fragrances, dyes, herbal extracts, and vitamins, provided that the selected additional component(s) is chemically and physically compatible. The term "compatible" is used herein to mean that the components of the compositions are capable of being combined with each other in a manner such that there is no interaction that would substantially reduce the efficacy of the compositions under ordinary use conditions. Some embodiments specifically include one or more of the herein disclosed additional ingredients, be they termed excipients, carriers, agents of specified function, or otherwise. Some embodiments specifically exclude one or more of the herein disclosed additional ingredients, be they termed excipients, carriers, agents of specified function, preservative, or otherwise.

According to some embodiments, the compositions comprise a polysorbate, e.g., polysorbate-20, polysorbate-40, polysorbate-80, or mixtures thereof.

The term "carrier" as used herein refers to a pharmaceutically acceptable inert agent or vehicle for delivering one or more active agents to a subject, and often is referred to as "excipient." The carrier must be of sufficiently high purity and of sufficiently low toxicity to render it suitable for administration to the subject being treated. The carrier further should maintain the stability and bioavailability of lipid-modified protein/cyclodextrin complexes disclosed herein. The carrier can be liquid or solid and is selected, with the planned manner of administration in mind, to provide for the desired bulk, consistency, etc., when combined with an active agent and other components of a given composition.

According to some embodiments, the described compositions comprise an aqueous carrier. The level and species of the carrier are selected according to the compatibility with other components, and other desired characteristic of the product. The aqueous carrier is contained in the compositions at a level by weight of, for example, about 30% to about 98%, about 50% to about 95%, or about 70% to about 95%.

Exemplary carriers include water and water solutions of lower alkyl alcohols. Exemplary lower alkyl alcohols include monohydric alcohols having 1 to 6 carbons, e.g., ethanol. According to some embodiments, the aqueous carrier is substantially water.

The pH of the described compositions are, for example, about 4 to about 8 When skin benefiting agents are included in the compositions, the pH may be adjusted to that which provides optimum efficacy. Buffers and other pH adjusting agents can be included to achieve the desirable pH. Exemplary pH adjusters herein include acetates, phosphates, citrates, triethanolamines and carbonates.

The viscosity (resistance to flow) of the described compositions may vary over a wide range, and may depend on viscosifying agents. For example, according to some embodiments, the described compositions may comprise a viscosifying agent that provides the compositions with a viscosity of from about 500 mPas to about 1,000,000 Pas. According to some embodiments, the viscosifying agent provides the compositions with a viscosity of about 1,000 mPas to about 100,000 mPas.

Carboxylic acid/carboxylate copolymers are nonlimiting examples of viscosifying agents used for providing microemulsions. Such copolymers can keep the composition at a suitable viscosity without being tacky or greasy upon use and can disperse and stabilize water insoluble components of the composition when such components are included. Exemplary commercially available carboxylic acid/carboxylate copolymers include acrylates/$C_{10-30}$ alkyl acrylate crosspolymers, e.g., PEMULEN™ TR-1, PEMULEN™ TR-2, CARBOPOL® 1342, CARBOPOL® 1382, and CARBOPOL® ETD 2020, all available from B. F. Goodrich Company.

Neutralizing agents, e.g., sodium hydroxide, potassium hydroxide, ammonium hydroxide, monoethanolamine, diethanolamine, triethanolamine, diisopropanolamine, aminomethylpropanol, tromethamine, tetrahydroxypropyl ethylenediamine, and mixtures thereof, may be included to neutralize the carboxylic acid/carboxylate copolymers.

Exemplary cellulose derivative polymers include, without limitation, methylcellulose, ethylcellulose, hydroxyethylcellulose, hydroxyethyl ethylcellulose, hydroxypropyl methyl cellulose, nitrocellulose, sodium cellulose sulfate, sodium carboxymethylcellulose, crystalline cellulose, cellulose powder, and mixtures thereof. According to some embodiments, the cellulose derivative polymers are hydroxyethylcellulose, carboxymethylcellulose, and mixtures thereof. Commercially available compounds that are highly useful herein include hydroxyethylcellulose with tradename Natrosol Hydroxyethylcellulose, and carboxymethylcellulose with tradename Aqualon Cellulose Gum, both available from Aqualon.

Other exemplary viscosifying agents include pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed (Cydonia oblonga Mill), starch (rice, corn, potato, wheat), and algae colloids (algae extract). Exemplary microbiological polymers include, without limitation, dextran, succinoglucan, starch-based polymers such as carboxymethyl starch, and methylhydroxypropyl starch. Exemplary alginic acid-based polymers include, without limitation, sodium alginate, and alginic acid propylene glycol esters. Exemplary acrylate polymers include, without limitation, sodium polyacrylate, polyacrylamide, and polyethyleneimine. Exemplary inorganic water soluble material includes, without limitation, bentonite, aluminum magnesium silicate, laponite, hectonite, and anhydrous silicic acid.

Polyalkylene glycols having a molecular weight of more than about 1000 also are exemplary viscosifying gents. Exemplary compounds include polyethylene oxides, polyoxyethylenes, and polyethylene glycols, polypropylene oxides, polyoxypropylenes, and polypropylene glycols; and polypropylene glycols and mixed polyethylene-polypropylene glycols, or polyoxyethylene-polyoxypropylene copolymers. Exemplary polyethylene glycol polymers include, without limitation, PEG-2M, also known as POLYOX WSR® N-10, which is available from Union Carbide and available as PEG-2,000); PEG-5M, also known as POLYOX WSR® N-35; and POLYOX WSR® N-80, both available from Union Carbide and as PEG-5,000 and Polyethylene Glycol 300,000); PEG-7M, also known as POLYOX WSR® N-750 (available from Union Carbide); PEG-9M, also known as POLYOX WSR® N-3333 (available from Union Carbide); and PEG-14 M, also known as POLYOX WSR® N-3000 available from Union Carbide).

Exemplary commercially available additional water soluble polymers include, without limitation, xanthan gum (KELTROL™, available from Kelco), Carbomers (CARBOPOL™ 934, CARBOPOL™ 940, CARBOPOL™ 950, CARBOPOL™ 980, and CARBOPOL™ 981 (all available from B. F. Goodrich Company), acrylates/steareth-20 methacrylate copolymer (ACRYSOL™ 22 (available from Rohm and Hass), polyacrylamide (SEPIGEL™ 305 (available from Seppic), glyceryl polymethacrylate (LUBRAGEL™ NP, and a mixture of glyceryl polymethacrylate, propylene glycol and PVM/MA copolymer (LUBRAGEL™ OIL (available from ISP), scleroglucan (CLEAROGEL™ SCI I available from Michel Mercier Products Inc. (NJ, USA)), ethylene oxide and/or propylene oxide based polymers (CARBOWAX™ PEGs, POLYOX™ WASRs, and UCON™ FLUIDS (all supplied by Amerchol).

Other exemplary agents include commercially available amphoteric polymers such as Polyquaternium 22 (MERQUAT™ 280, MERQUAT™ 295), Polyquaternium 39 (MERQUAT™ PLUS 3330, MERQUAT™ PLUS 3331), and Polyquaternium 47 (MERQUAT™ 2001, MERQUAT™ 200 IN), all available from Calgon Corporation.

The term "humectants" as used herein refers to substances that promote water retention due to their hygroscopicity. They act by being absorbed into the skin and attract water from the atmosphere. The attracted water then serves as a reservoir for the stratum corneum.

Exemplary water-soluble humectants include, without limitation, polyhydric alcohols, such as butylene glycol (1,3 butanediol), pentylene glycol (1,2-pentanediol), glycerin, sorbitol, propylene glycol, hexylene glycol, ethoxylated glucose, 1,2-hexane diol, 1,2-pentane diol, hexanetriol, dipropylene glycol, erythritol, trehalose, diglycerin, xylitol, maltitol, maltose, glucose, fructose; and other water-soluble compounds such as urea, sodium chondroitin sulfate, sodium hyaluronate, sodium adenosin phosphate, sodium lactate, pyrrolidone carbonate, glucosamine, cyclodextrin, and mixtures thereof. Additional examples include water soluble alkoxylated nonionic polymers such as polyethylene glycols and polypropylene glycols of molecular weight of up to about 1000 (e.g., PEG-200, PEG-400, PEG-600, PEG-1000), and mixtures thereof.

Commercially available humectants include, without limitation: butylene glycol (1,3-Butylene glycol, available from Celanese), pentylene glycol (HYDROLITE™-5 available from Dragoco), glycerin (STAR™ and SUPEROL™, available from The Procter & Gamble Company, CRODEROL™ GA7000 available from Croda Universal Ltd., PRECERIN™ series available from Unichema, and a same tradename as the chemical name available from NOF; propylene glycol (LEXOL™ PG-865/855 available from Inolex, 1,2-PROPYLENE GLYCOL USP available from BASF; sorbitol (LIPONIC™ series available from Lipo, SORBO™, ALEX™, A-625™, and A-641™ available from ICI, and UNISWEET™ 70, UNISWEET™ CONC available from UPI; dipropylene glycol with the same tradename available from BASF; diglycerin (DIGLYCEROL™, available from Solvay GmbH); xylitol with the same tradename available from Kyowa and Eizai; maltitol (MALBIT™ available from Hayashibara; sodium chondroitin sulfate with the same tradename available from Freeman and Bioiberica, and with tradename ATOMERGIC SODIUM CHONDROITIN SULFATE available from Atomergic Chemetals; sodium hyaluronate, available from Chisso Corp. the same with tradenames ACTIMOIST™ available from Active Organics, AVIAN SODIUM HYALURONATE series, available from Intergen, HYALURONIC ACID Na, available from Ichimaru Pharcos; sodium adenosine phophate with the same tradename available from Asahikasei, Kyowa, and Daiichi Seiyaku; sodium lactate with the same tradename available from Merck, Wako, and Showa Kako, cyclodextrin (CAVITRON™ available from American Maize, RHODOCAP™ series available from Rhone-Poulenc, and DEXPEARL™ available from Tomen); polyethylene glycols (CARBOWAX™ series available from Union Carbide), and a mixture of glyceryl polymethacrylate, propylene glycol and PVM/MA copolymer (LUBRAJEL™ Oil available from Guardian Lab).

The term "preservative" is used herein to refer to substances that prevent or inhibit the growth of undesired microorganisms in products that contain water. Preservatives approved for use in pharmaceuticals, such as topical formulations, may be identified in the current Federal Regulations published in volume 21 of the Code of Federal Regulations, which is incorporated herein by reference. Exemplary preservatives include, without limitation: ascorbic acid, ascorbyl palmitate, biopein, BHT (butylated hydroxyl-toluene), butylated hydroxyanisole, butylated hydroxytoluene, butylparaben, calcium ascorbate, calcium sorbate, citric acid, cinnamon cassia, chlorocresol, diazolidinyl urea, dilauryl thiodipropionate, EDTA (ethylenediamine tetraacetic acid tetrasodium salt), erythorbic acid, grapefruit seed extract, hydroxybenzoates, methylparaben, Neopein, phenonip, phenoxyethanol, potassium bisulfite, potassium metabisulfite, potassium sorbate, propylparaben, rosemary oil extract, sodium ascorbate, sodium benzoate, sodium bisulfite, sodium metabisulfite, sodium sorbate, sodium sulfite, sorbic acid, sulfur dioxide, Suprarein, thiodipropionic acid, silver particles, and/or tocopherols. Additionally, preservation may also be accomplished by storage of the cyclodextrin/lipid-modified protein complex or a composition or formulation comprising the complexes at reduced temperatures (e.g., below 4° C., or frozen).

In some embodiments, the compositions are applied topically once daily, twice daily, three times daily, every other day, weekly, or for any time period necessary to achieve the desired results. Typically, the compositions are applied topically to the desired treatment area and allowed to absorb into the skin Therapeutic Uses Therapeutic uses for the cyclodextrin/lipid-modified protein complex-containing compositions include but are not limited to tissue regeneration.

The compositions and formulations disclosed herein can be administered topically. Cyclodextrin complex-containing compositions can be topically administrated in doses containing about 0.1% to about 100% of the harvesting solution. In certain embodiments, the compositions are administered topically at a dose of about 5% to about 25% (v/w, v/v or w/v), about 10% to about 25%, about 15% to about 25%, about 20% to about 25%, about 5% to about 20%, about 5% to about 15%, about 5% to about 10%, about 5%, about 7.5%, about 10%, about 12.5%, about 15%, about 17.5%, about 20%, about 22.5%, or about 25% or any range bounded by these values.

Dosages and desired drug concentrations of compositions disclosed herein may vary depending on the particular use envisioned. The determination of the appropriate dosage is well within the skill of an ordinary physician. Animal experiments provide reliable guidance for the determination of effective doses for human therapy. Interspecies scaling of effective doses can be performed following the principles laid down by Mardenti, J. and Chappell, W. "The use of interspecies scaling in toxicokinetics" In Toxicokinetics and New Drug Development, Yacobi et al, Eds., Pergamon Press, New York 1989, pp. 42-96. The term "therapeutically effective" amount as used herein refers to the amount needed to perform the particular treatment such as, for example, hair growth. "Treatment" refers to both therapeutic treatment and prophylactic or preventative measures, wherein the object is to prevent or slow down (lessen) the targeted condition or disorder. Those in need of treatment include those already with the disorder as well as those prone to have the disorder or those in whom the disorder is to be prevented. In some embodiments, the disorder is present.

Uses for the cyclodextrin/lipid-modified ligand complex include, but are not limited to, cardiac muscle regeneration, lung regeneration, wound healing, restoration of tactile sensation, restoration of gustative sensation, accelerated osteogenesis after fractures, in vitro oocyte maturation, peripheral and central neural tissue regeneration, breast tissue regeneration or augmentation, penile size augmentation, sensorial tactile augmentation of the external genital organs, accelerated revascularization of transplants, immunomodulation, treatment of neurodegenerative disease, brain regeneration, liver regeneration, spinal cord regeneration, or reproductive organ regeneration. In certain embodiments, the tissue regeneration is in any tissue other than skin or hair.

In some embodiments, the cyclodextrin/lipid-modified ligand complex is suitable for restoration of sensory nerve function in a tissue in need thereof. In some embodiments, the tissue is a central nervous system tissue or a peripheral nervous system tissue.

Also disclosed herein is use of the cyclodextrin/lipid-modified ligand complexes for treating a neurodegenerative disorder comprising administration of a composition disclosed herein to a subject in need thereof. In some embodiments, the neurodegenerative disorder is Alzheimer's disease, Parkinson's disease, spinal cord injury, brain injury, peripheral nerve injury, peripheral neuropathy, multiple sclerosis, amyotrophic lateral sclerosis, or dementia.

Some regenerative uses have a cosmetic aspect to them, particularly when applied to skin and hair. Such uses include the reduction of age-related spotty pigmentation, wrinkles, and balding. In some embodiments directed to a reduction in balding, the patients have mild to moderate pattern hair loss, for example grade I or II for women according to the Ludwig classification or grade III or IV for men according to the Norwood classification. In other embodiments the patients have greater hair loss. In various embodiments, treatment results in a reduction in grade by at least 1, 2, 3, or more steps according to the appropriate classification.

The term "treating" or "treatment" broadly includes any kind of treatment activity, including the mitigation, or prevention of disease in man or other animals, or any activity that otherwise affects the structure or any function of the body of man or other animals. Treatment activity includes the administration of the medicaments, dosage forms, and pharmaceutical compositions described herein to a patient, especially according to the various methods of treatment disclosed herein, including for example, methods of promoting tissue regeneration, whether by a healthcare professional, the patient his/herself, or any other person. Treatment activities include the orders, instructions, and advice of healthcare professionals such as physicians, physician's assistants, nurse practitioners, and the like that are then acted upon by any other person including other healthcare professionals or the patient his/herself. In some embodiments, treatment activity can also include encouraging, inducing, or mandating that a particular medicament, or combination thereof, be chosen for treatment of a condition—and the medicament is actually used—by approving insurance coverage for the medicament, denying coverage for an alternative medicament, including the medicament on, or excluding an alternative medicament, from a drug formulary, or offering a financial incentive to use the medicament, as might be done by an insurance company or a pharmacy benefits management company, and the like. In some embodiments, treatment activity can also include encouraging, inducing, or mandating that a particular medicament be chosen for treatment of a condition—and the medicament is actually used—by a policy or practice standard as might be established by a hospital, clinic, health maintenance organization, medical practice or physicians group, and the like.

Embodiments directed to treatment are generally phrased as methods of treatment, but for each such embodiment there are parallel embodiments styled as use of a composition in medicine, use of a composition in the manufacture of a medicament, and a composition for use in medicine. In various embodiments, medicine, medicament, and similar terminology should be understood to refer to pharmaceuticals and cosmeceuticals, either individually or as a group, and their related uses.

EXAMPLES

Example 1. Capture and Detection of Hh/Wnt from Cells Derived from Partially Differentiated Embryonic Stem Cell Cultures Embryonic stem cells were expanded according to current published methods using a serum free media supplemented with bFGF (10 ng/mL) and activin A (5 ng/mL) on an adherent substrate consisting on a thin layer of MATRIGEL®. After confluence, half of the cultures were fed with the same media not including the growth factors bFGF and Activin A. A cell culture supernatant sample was analyzed for follistatin concentration.

Individual cultures, undifferentiated or partially differentiated, were exposed to 10 mM solution of α-cyclodextrin, β-cyclodextrin, γ-cyclodextrin, or methyl-β-cyclodextrin (MBCD) for 60 min to 180 min. The cell cultures before exposure observed under phase contrast microscopy were adherent to the cell culture vessel surface, smooth, compact, with areas of monolayer or multilayered cells. After incubation with a cyclodextrin, the cultures were disrupted with the majority of cells losing adherence. Under phase contrast microscopy the previously adherent cell layers were dissociated in single cells, or patches of multiple cells freely floating in media.

The MBCD solution incubated with the cells was then analyzed for the concentration of SHh, Wnt 3a, and Wnt7a. The results are presented in Table 3.

TABLE 3

Concentration of follistatin in the supernatant media of the cell culture prior exposure to cyclodextrins and the concentration of Wnt and SHh in the methyl-beta-cyclodextrin capture solution after 3 hr exposure to the cell culture.

|  | Undifferentiated hESC (ng/mL) | Partial differentiated hESC (ng/mL) | Media control |
|---|---|---|---|
| Follistatin (in supernatant) | 0.830 | 9.562 | 0 |
| Wnt3a | 7.950 | 7.720 | 0 |
| Wnt7b | 27.026 | 24.658 | 0 |
| SHh | 0.000 | 570.900 | 0 |

Addition of α- or β-cyclodextrin demonstrated a reduced but proportional effect to that observed with MBCD.

The identical preparation of cells and cyclodextrin solution produced from 3 different experiments were analyzed by multiplex ELISA for a panel of about 400 target proteins. The results are provided in Table 4, that include the detected proteins in significant concentration.

TABLE 4

The following proteins were detected in large amounts, over 100 pg/mL:

| Protein | pg/mL |
|---|---|
| Fetuin A | 271841.19 |
| CD48 | 86293.07 |
| Ferritin | 68029.27 |
| CD58 | 44081.91 |
| PAI-1 | 34971.90 |
| CD155 | 26687.22 |
| MIF | 18101.91 |
| MMP-9 | 13877.59 |
| NSE | 11606.19 |
| P-Cadherin | 10837.02 |
| DPPIV | 9965.87 |
| Periostin | 8431.51 |
| IGFBP-3 | 8274.76 |
| Testican 2 | 8255.61 |
| OPN | 8160.50 |
| Nidogen-1 | 7420.45 |
| hCGb | 7274.94 |
| Albumin | 6847.44 |
| GROa | 6739.24 |
| TFPI | 4982.39 |
| VEGF R1 | 4930.25 |
| Midkine | 4928.33 |
| ADAM8 | 4705.57 |
| Decorin | 4531.33 |
| sFRP-3 | 3823.44 |
| Pref-1 | 3739.18 |
| IGFBP-2 | 3311.37 |
| WISP-1 | 3043.28 |
| bIG-H3 | 2797.74 |
| AFP | 2797.68 |
| Follistatin | 2445.43 |
| TIMP-2 | 2420.03 |
| Desmoglein 2 | 2170.15 |
| TSP-1 | 2135.90 |
| Chemerin | 2104.45 |
| IGFBP-6 | 1901.18 |
| MMP-1 | 1853.63 |
| Cadherin-4 | 1851.69 |
| EMMPRIN | 1793.35 |
| Contactin-2 | 1543.63 |
| ICOS | 1520.81 |
| DR3 | 1434.87 |
| Dkk-3 | 1419.26 |
| TIMP-1 | 1409.77 |
| SLAM | 1401.11 |
| Cystatin B | 1400.10 |
| Pentraxin 3 | 1235.59 |
| ErbB3 | 1114.29 |
| IGFBP-4 | 1004.54 |
| BMPR-IB | 963.78 |
| Cystatin E M | 957.94 |
| Galectin-2 | 935.23 |
| GDF-15 | 906.42 |
| Legumain | 878.59 |
| B2M | 796.32 |
| JAM-B | 795.24 |
| Syndecan-4 | 791.02 |
| CFXIV | 786.29 |
| ESAM | 733.20 |
| Cathepsin L | 714.51 |
| aFGF | 695.13 |
| Siglec-10 | 576.65 |
| BCAM | 546.72 |
| Syndecan-1 | 514.45 |
| ICAM-1 | 494.64 |
| TNF RI | 470.87 |
| FOLR1 | 462.51 |
| BMPR-IA | 447.85 |
| Cadherin-13 | 446.01 |
| Dtk | 434.66 |
| HAI-2 | 425.01 |
| IL-9 | 399.69 |
| Galectin-1 | 396.89 |
| Cathepsin B | 373.42 |
| MMP-2 | 368.54 |
| bFGF | 353.19 |
| Insulin | 346.45 |
| G-CSF R | 335.75 |
| Angiostatin | 275.81 |
| IL-1 F6 | 272.18 |
| GCP-2 | 258.59 |
| ENA-78 | 255.88 |
| CXCL16 | 244.42 |
| CEACAM-5 | 236.16 |
| NOV | 227.24 |
| MCP-1 | 221.95 |
| PSMA | 220.95 |
| CHI3L1 | 216.69 |
| HGF R | 214.68 |
| Serpin A4 | 197.65 |
| Angiogenin | 184.54 |
| Clusterin | 183.44 |
| NCAM-1 | 178.32 |
| Thrombomodulin | 163.37 |
| Dkk-4 | 159.88 |
| CA19-9 | 147.14 |
| ANG-4 | 145.77 |
| B7-H3 | 144.59 |

TABLE 4-continued

The following proteins were detected in large amounts, over 100 pg/mL:

| Protein | pg/mL |
| --- | --- |
| Thrombospondin-2 | 142.16 |
| BMP-5 | 140.88 |
| Resistin | 135.83 |
| ADAM12 | 134.22 |
| LRP-6 | 130.00 |
| GRO | 129.80 |
| LAP(TGFb1) | 128.40 |
| TLR4 | 126.64 |
| SP-D | 118.46 |
| EpCAM | 114.94 |
| Pepsinogen I | 114.00 |
| TGFb1 | 113.26 |
| Gas 1 | 110.63 |
| Cripto-1 | 109.78 |
| gp130 | 104.84 |

The following proteins were detected in small amounts, ranging between 10-100 pg/mL: RBP4, ANGPTL4, MMP-10, IL-21, MMP-7, ALCAM, Activin A, Fcg RIIBC, ULBP-1, DKK-1, SCF R, TNF RII, IL-5 Ra, IL-1 F9, PDGF-AA, LDL R, uPAR, Furin, TIM-3, Epo R, EGF R, MMP-13, PDGF-BB, JAM-A, CD99, TGFb2, IL-13 R1, PIGF, GH, Cystatin C, Kallikrein 5, Adipsin, TWEAK, TF, HGF, Transferrin, Galectin-9, VEGF R3, CD229, ErbB4, BMP-4, NAP-2, E-Cadherin, ANG-2, IL-34, IL-6, LOX-1, NT-4, OPG, Axl, TRAIL R3, PF4, Lipocalin-2, IL-1ra, AR, IL-11, TIM-1, FGF-21, uPA, CA9, ANG-1, CD23, VEGF, IL-27, IL-6R, DLL1, IL-1a, RGM-B, MCSF, FGF-4, IGFBP-1, Tie-2, ICAM-2

The following proteins were detected in trace amounts, ranging between 0.1-10 pg/mL: BMP-7, IP-10, IL-15 R, TRAIL R2, RAGE, EG-VEGF, NrCAM, NGF R, IL-2 Ra, IL-1 R3, IL-13 R2, NT-3, IL-8, FAP, Leptin R, LIF, IL-16, TNFb, Renin, LYVE-1, MCSF R, MDC, I-TAC, IL-17E, Trappin-2, TNFa, IL-15, Aggrecan, VEGF R2, SCF, TGFa, IL-2, IL-17B, IFNg, Galectin-7, MICA, IL-31, 1-309, ICAM-3, b-NGF, FAS L, TARC, Cathepsin S, VEGF-D, MCP-4, MIP-3a, PDGF-AB, MEPE, MCP-2, TSLP, MIP-1b, MIP-1d, AgRP, BLC, IL-12p40, EGF, SDF-1a, IL-7, IL-17F, MCP-3, TRAIL, FGF-7, GM-CSF The following proteins were not detected: IL-7, IL-17F, MCP-3, TRAIL, FGF-7, GM-CSF, Prostasin, IL-10, GDNF, IL-13, IL-12p70, 2B4, 4-1BB, ADAM9, ADAMTS13, Adiponectin, ANGPTL3, B7-1, B7-H1, CD14, CD200, CD30, CD40, CD40L, CD97, Ck beta 8-1, CNTF, DAN, DcR3, DR6, Endoglin, Eotaxin, ErbB2, E-Selectin, FABP2, Fas, FGF-19, FLRG, Flt-3L, Fractalkine, Galectin-3, GITR, GITR L, Granulysin, HVEM, IGF-1, IGF-1R, IGF-2, IL-1 F10, IL-1 F5, IL-1 F8, IL-1 R5, IL-1 R6, IL-1 RI, IL-10 Rb, IL-17, IL-17R, IL-1b, IL-2 Rg, IL-20, IL-21R, IL-32 alpha, L1CAM-2, Leptin, LIMPII, LRIG3, Marapsin, MBL, MICB, MIG, Nectin-4, NRG1-b1, Osteoactivin, PDGF Rb, PECAM-1, Persephin, Prolactin, RANK, ROBO3, S100A8, Siglec-5, Siglec-7, Siglec-9, SOST, Syndecan-3, TACI, TGFb3, Thrombospondin-5, Tie-1, TLR2, VCAM-1, WIF-1, XEDAR, G-CSF, TRAIL R4, TREM-1, IL-18 Rb, MMP-8, ST2, CRP, ULBP-2, GASP-1, CTLA4, RANTES, PSA-free, IL-3, CEACAM-1, SDF-1b, IL-23, HCC-1, OSM, CTACK, CEA, MMP-3, MIP-3b, IL-18 BPa, Troponin I, BAFF, TSH, FSH, IL-1 RII, Eotaxin-3, IL-28A, TECK, ACE-2, TPO, PARC, BCMA, TACE, Lymphotactin, TRANCE, Cystatin A, HCC-4, BTC, AMICA, CCL28, IL-29, TIMP-4, LIGHT, CXCL14, Procalcitonin, CA15-3, MPIF-1, IGFBP-5, Angiotensinogen, IL-17B R, GASP-2, L-Selectin, Thyroglobulin, MSP, VE-Cadherin, 6Ckine, CD84.

Example 2. Cell Source and Harvesting Method

To test the differences between differentiation status of the cells and beta-cyclodextrin chemical modification, we harvested membrane bound signals from partially differentiated and pluripotent stem cells cultures and using two different beta-cyclodextrins: methyl and hydroxypropyl modified.

Embryonic stem cell cultures were maintained until confluence in four identical culture vessels. At confluence, two of the cultures were harvested at the non-differentiated stage, using 15 mL/75 cm$^2$ of 20% trehalose and 10 mM methyl-beta-cyclodextrin or hydroxypropyl-beta-cyclodextrin solutions, overnight.

The other two cultures underwent differentiation in serum free, growth factor free media for two days, then harvested using identical methods with methyl-beta-cyclodextrin or hydroxypropyl-beta-cyclodextrin solutions.

After two days in the given conditions the embryonic stem cells underwent partial differentiation into a mixture of ectoderm and mesoderm lineages. This mixture of lineages reassembles the early development.

The extracts were stored at 4° C. until analysis.

The analysis was conducted with quantitative ELISA kits for Wnt3a (HUM-WNT-3A) and Sonic Hedgehog (HUM-SHh N-Terminus) per manufacturer's specifications.

The nondifferentiated stem cells (ES) produced less Wnt-3A than the differentiated cells (DIF). The methyl-beta-cyclodextrin (MBCD) performed better extraction than the hydroxypropyl-beta-cyclodextrin (HPCD).

TABLE 5

Comparison of amounts of Wnt-3A extracted by methyl-beta-cyclodextrin (MBCD) and hydroxypropyl-beta-cyclodextrin (HPCD) on nondifferentiated stem cells (ES) and partial differentiated cells (DIF)

| Preparation | Mean concentration (ng/mL) | Standard error |
| --- | --- | --- |
| ES-MBCD | 15.086 | 1.615 |
| DIF-MBCD | 16.921 | 1.807 |
| ES-HPCD | 10.932 | 1.251 |
| DIF-HPCD | 7.120 | 0.391 |

Sonic hedgehog was present in much higher quantity on partial differentiated stem cells (DIF) and better extracted with methyl-beta-cyclodextrin (ME-CDX).

TABLE 6

Comparison of amounts of SHh extracted by methyl-beta-cyclodextrin (MBCD) and hydroxypropyl-beta-cyclodextrin (HPCD) on nondifferentiated stem cells (ES) and partial differentiated cells (DIF)

| Preparation | Mean concentration (ng/mL) | Standard error |
| --- | --- | --- |
| ES-MBCD | 5.164 | 0.612 |
| DIF-MBCD | 20.540 | 0.672 |
| ES-HPCD | 2.924 | 0.449 |
| DIF-HPCD | 5.745 | 0.541 |

In conclusion, the data suggests that the membrane bound growth factor (Wnt, SHh) extraction is more effective with methyl-beta-cyclodextrin. In addition, the partially differentiated cells provided higher concentrations of the extracts.

Example 3. Comparison Study for Hair Growth in an Animal Model

A culture of partial-differentiated embryonic stem cells was exposed to a harvest solution containing 10 mM methyl-β-cyclodextrin and 20% trehalose in water for injection, at a volume of 1 mL/$10^6$ cells for 3 hours at room temperature to obtain the cyclodextrin/lipid-modified protein complexes subsequently referred as "active ingredient".

The formulated active ingredient (containing phenoxyethanol and caprylyl glycol 0.75% as preservative) was tested targeting hair growth (or re-growth). A mouse model for hair growth was used to test a prototype formulation. Male and female mice 6 weeks of age in confirmed first telogen phase were randomized in the treatment groups for 3 different concentrations and a negative control.

On Day −1, all the animals were anesthetized with isoflurane and the entire back (from shoulders to haunches) was freed of hair by clippers. The test articles were applied topically for 14 days continuously starting on Day 0; test articles were rubbed gently into the dorsal skin of each mouse daily. New gloves were worn for each treatment type. Animals were single housed during treatment period to avoid cage-mates licking the test article.

Body weights and clinical observations were measured weekly. Macroscopic digital photographs were taken on Days 2, 7, 10, 14, and 22 On Day 22, skin samples from all mice were collected and fixed in formalin for histology analysis.

Figure 7B:
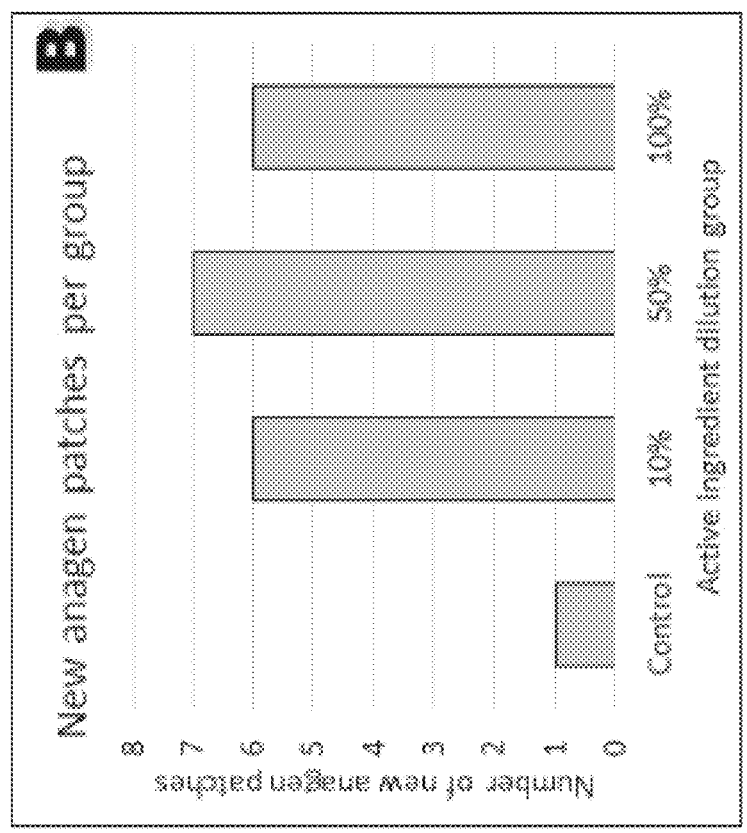
FIGS. 7A-C are graphs of quantitated responses to treatment based on photographs such as those in FIGS. 6A-D.
Figure 7A:
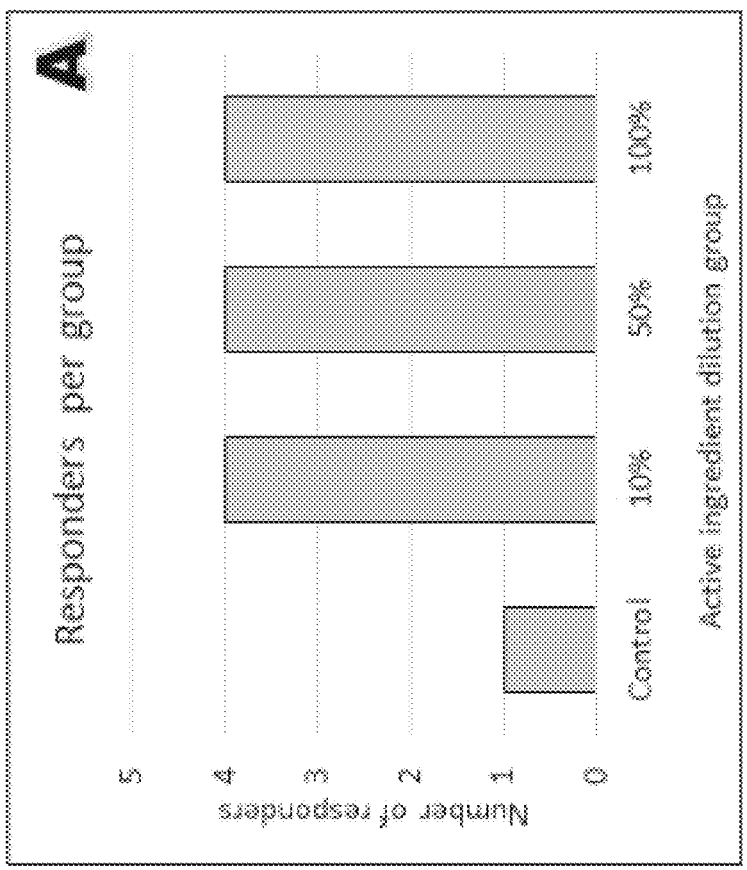
Figure 7C:
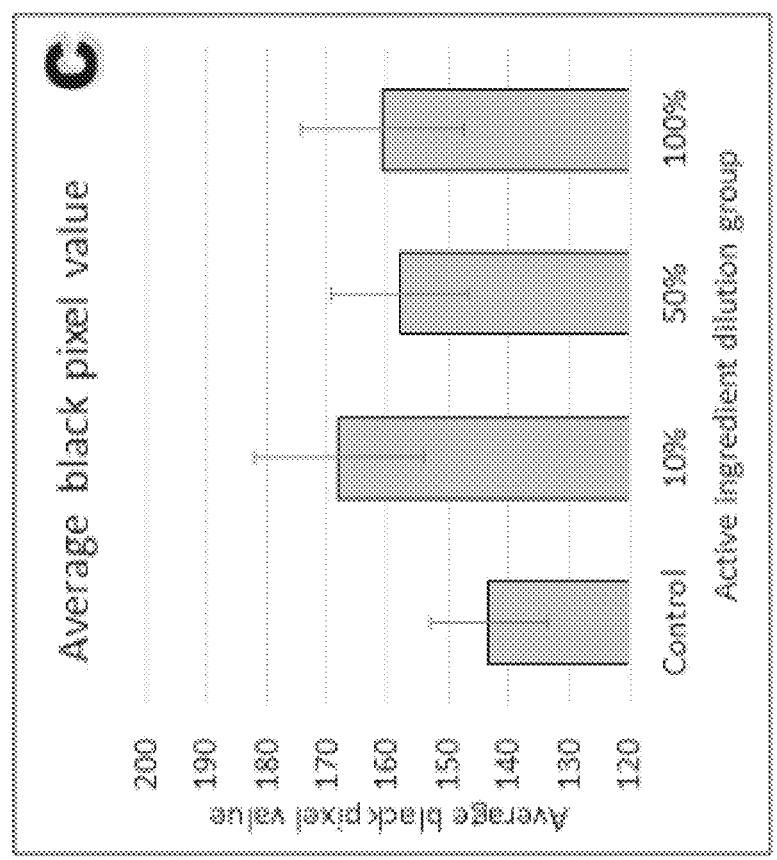

All treated groups displayed new anagen patches in 80% of subjects regardless of concentration of active ingredient compared to 20% in the control group. The response confirmed by increased darkness of the skin by 11.3%, 13.4 and 19.01% in the treatment groups compared to the control group evaluated by the black pixel count of the standardized photographs. The count of new anagen patches in the shaved area was 6 to 7 patches per animal in the treated groups and 1 patch in one of the animals in the control group (FIGS. 7A-C)

Figure 10C:
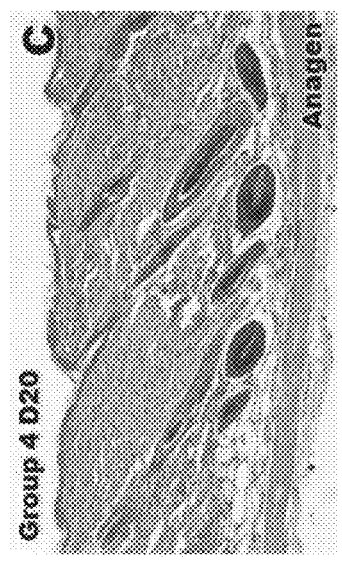
FIGS. 10A-C depict hair growth in treated mice. The mice in all treatment groups (Groups 2, 3 and 4.
Figure 10B:
Figure 10A:

Hematoxylin and eosin staining of the histological sections obtained at day one of the study demonstrate the telogen onset and persistence of hair follicles in telogen at the end of the study in the control group (FIG. 8). At the end of the study, the hematoxylin and eosin staining of histological sections of the skin shows that the mice in the treatment groups display telogen to anagen transition, suggested by a mix of telogen and early anagen (EA) follicles in the areas that do not display yet visible hair growth (FIG. 9) and typical anagen hair follicle morphology in the new hair patches (FIG. 10).

Figures 12A, 12B, 12C:
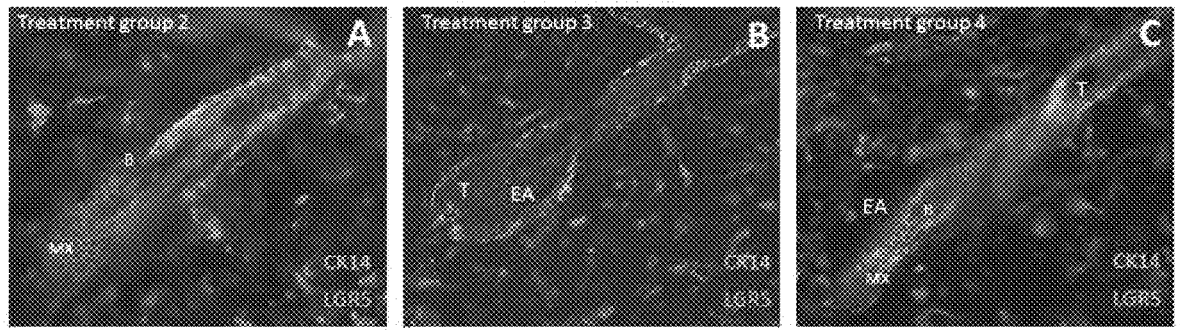
FIGS. 12A-I depict grayscaled images of hair follicles in treated mice.
Figures 12D, 12E, 12F:
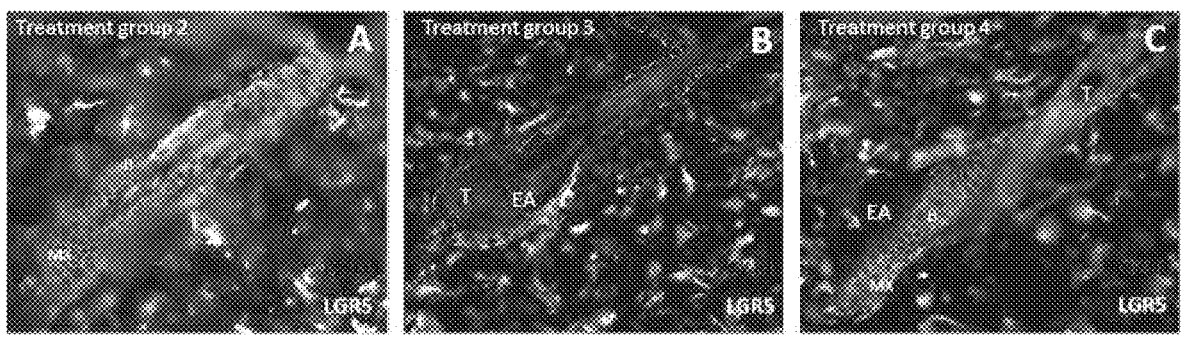
Figures 12G, 12H, 12I:
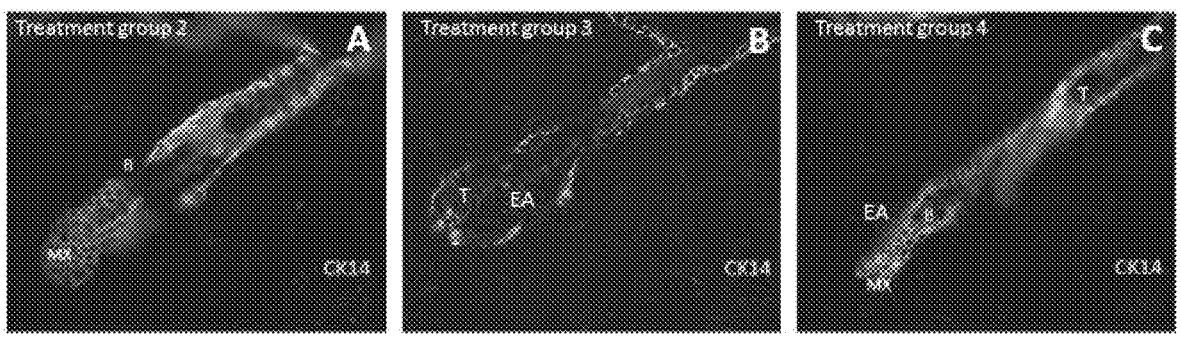

In telogen phase, the hair follicle stem cells are dormant localized in the bulge area of the old follicle. LGR5 is a putative hair follicle stem cell marker that is Wnt induced. LGR5+ cells fuel the actual hair follicle shaft upon migration into the dermal papilla during transition to anagen. Under immunofluorescence microscopy, in the samples from control group LGR5 expression was found minimal or absent along the CK14 positive basal cells marking the outer root sheath of the hair follicle (FIG. 11). In treated groups, Wnt signaling induced LGR5 demonstrating hair follicle stem cell activation and the transition to a new anagen phase (FIG. 12).

Figure 13B:
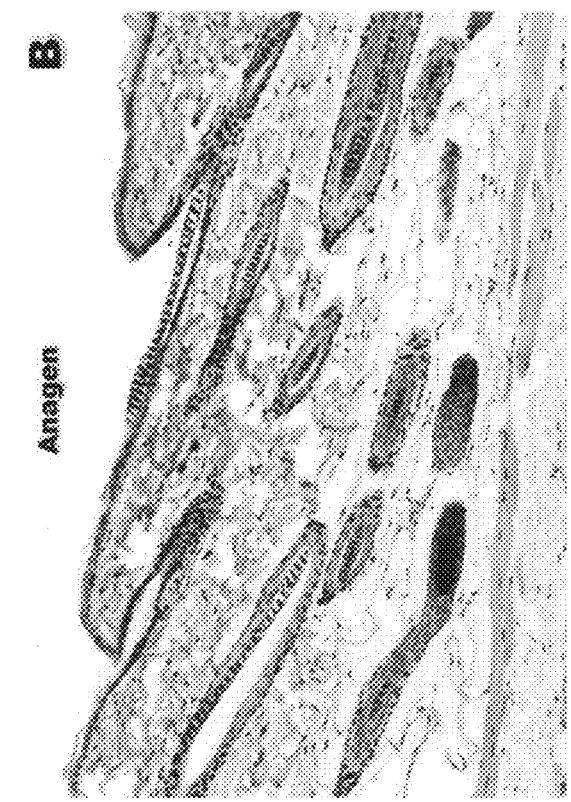
FIGS. 13A-B depict hair growth in treated animals. The treated animals show hair stem cell mobilization by Sox9 positivity.
Figure 13A:

SOX9 is a pioneer factor governing hair follicle stem cell fate and plasticity, essential for outer root sheath (ORS) differentiation and the formation of the hair stem cell compartment in the bulge. Sox9 expression depends on sonic hedgehog (SHh) signaling. The treated animals show hair stem cell mobilization by Sox9 positivity in the anagen induced hair follicle matrix (FIG. 13).

Example 4. Ex Vivo Human Hair Follicle Cultures

Figure 14A:
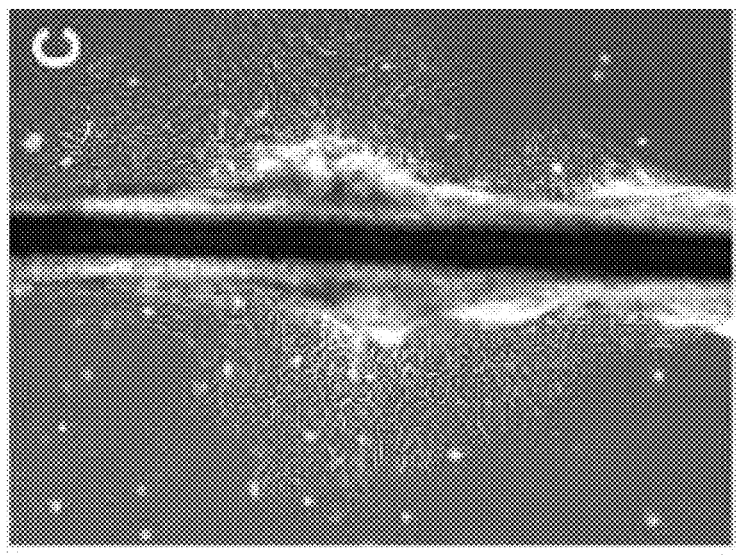
Figure 14B:
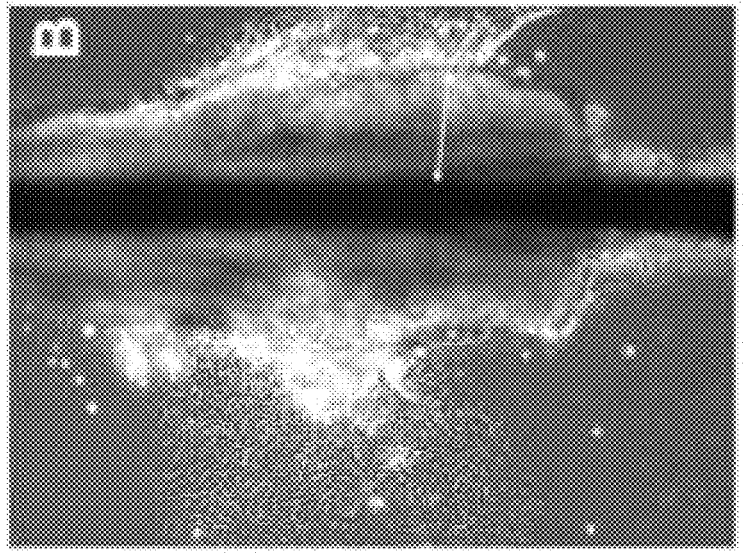
Figure 14C:
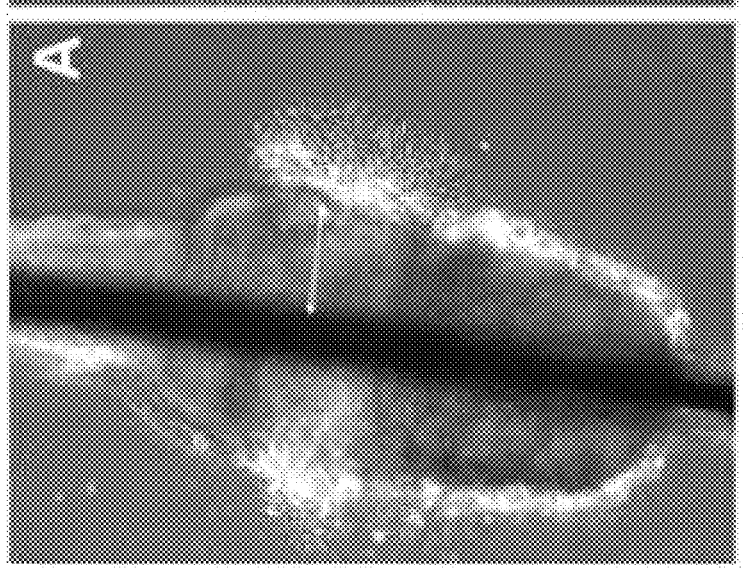

Plucked human hair with evident presence of the bulb area were immersed immediately after collection in cell growth media. Some of the hair samples were exposed to with lipid-modified protein/MBCD complexes (loaded MBCD) from embryonic stem cell culture as described in Example 2 (referred to as active ingredient), or unloaded MBCD as control, at the same concentration of 0.25 mM of the cyclodextrin component. No other growth factors (e.g., EGF, KGF, etc) were used in the hair follicle cultures. After 2 days in culture (FIG. 14A-C), attachment and a small outgrowth of cells was observed under phase contrast microscopy in both MBCD-containing and control follicle cultures, with more outgrowth in those follicle cultures containing the MBCD-loaded factors. After 5 days of exposure (FIG. 14D-G), the control follicles underwent senescence and detached from the substrate, while the follicle cultures exposed to MBCD increased diameter by about 80% and continued the cell outgrowth to the cell culture vessel surface.

Human hair follicles from a non-balding man were dissected out of scalp samples. A total of 15 hair follicles per group were transferred in standard DMEM:F12 with 5% fetal bovine serum culture media and exposed to either the control or the active ingredient at concentrations of 0.1 mM, 0.25 mM or 0.5 mM of the cyclodextrin component. Hair length and hair follicle thickness were measured on days 0 and 7.

Figure 15A:
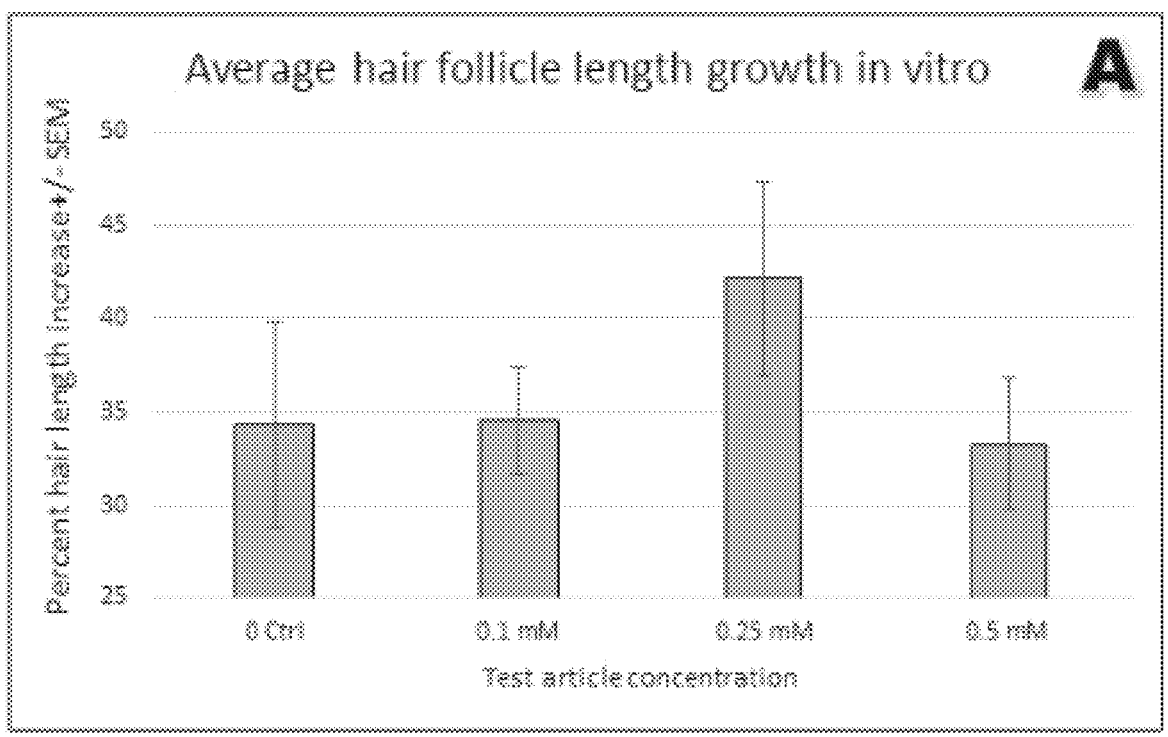
FIGS. 15A-B depict quantitation of hair follicle length and thickness, respectively upon the indicated treatment. 15A depicts hair follicles displaying enhanced growth in length grown in 0.25 mM MBCD complex.
Figure 15B:
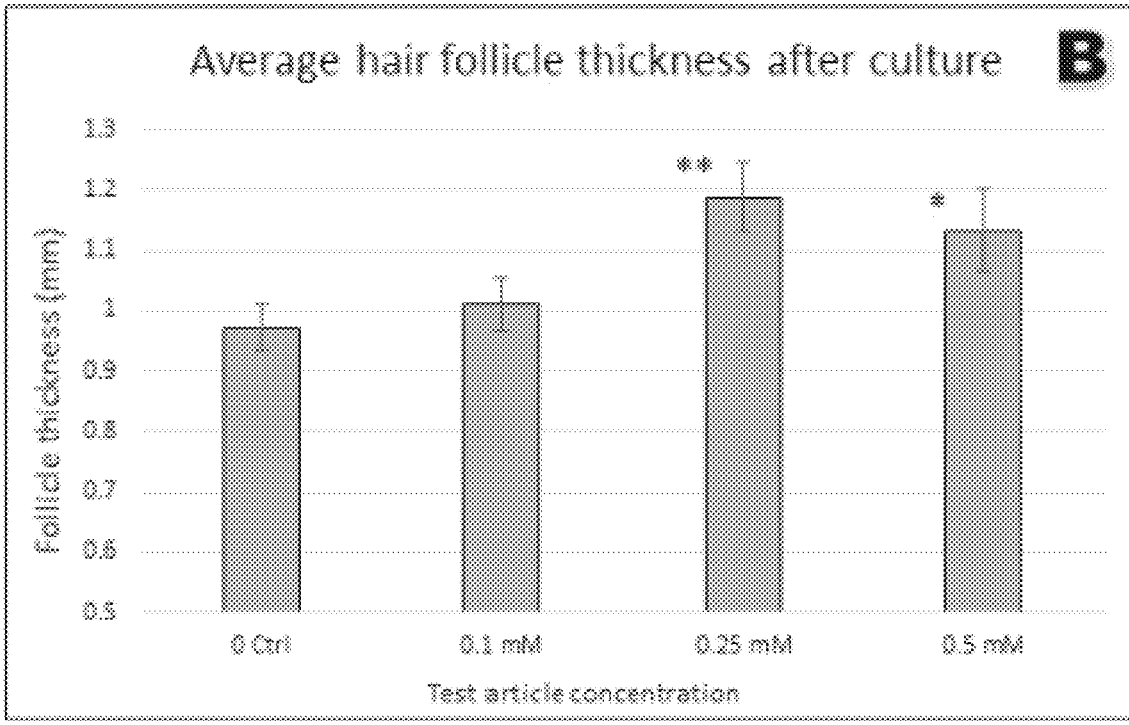

Within 7 days, most of the hair follicles grew in length, resulting in an increase in legnth from 0 to 63%. Hair follicles treated with 0.25 mM active ingredient grew 42%+/−13, while follicles in the other treatment grew 33 to 34%. The same test condition reached statistical significance in follicle thickness growth, $p<0.01$ for 0.25 mM and $p<0.05$ for the 0.5 mM group (FIGS. 15A-B).

Figure 16A:
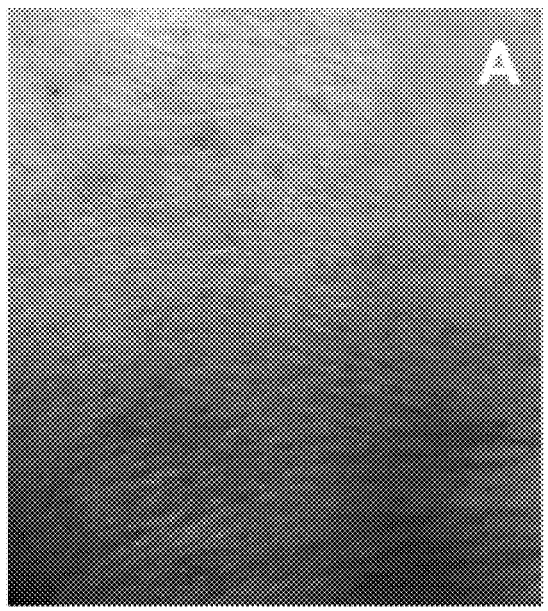
FIG. 16A-D depicts the testing on human skin of a composition containing MBCD loaded with embryonic stem cell membrane components and trehalose.
Figure 16B:
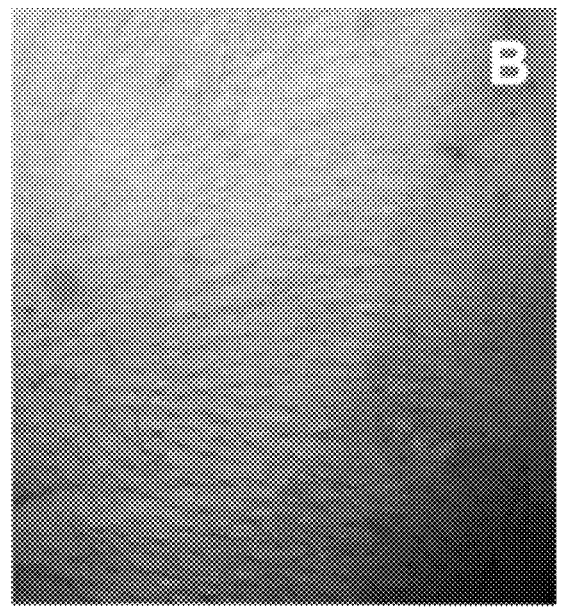
Figure 16C:
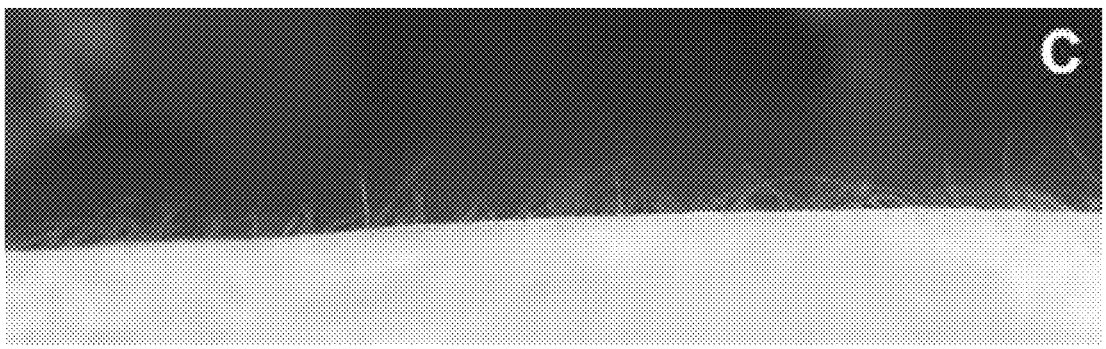
Figure 16D:
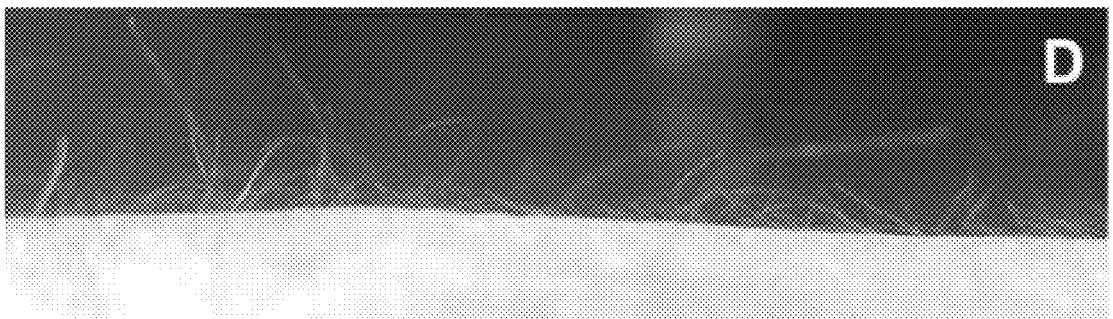

Example 5. Clinical Testing of Formulation Containing Cell Membrane-Bound Lipid Modified Signaling Factors An active ingredient consisting of cyclodextrin/lipid-modified protein complexes was produced by exposing a culture of partial differentiated human embryonic stem cells to a harvest solution containing 10 mM methyl-β-cyclodextrin and 20% trehalose in water for injection, 1 mL/$10^6$ cells, for 3 hours at room temperature. The composition was applied externally on the dorsal area of the wrist joint of one hand, while the other hand was left untreated. This section of the hand is covered with terminal arm velus hair with identical left and right pattern and density, however with evident signs of telogen due to mechanical wear. The application consisted of about 1 drop (30 µL) that was spread across the skin, allowed to dry until tackiness, then rubbed until tackiness disappeared. The area was treated daily for 5 days and evaluated after 2 weeks. The growth of the terminal arm hair is clearly accentuated in the treated area (FIG. 16C-D). In addition, the age-related wrinkles and spotty pigmentations were clearly reduced, and the skin texture improved. The improvement of the tactile sensation was reported by the subject by increasing the 2-point discriminative ability. The observations suggest a rejuvenating effect on the skin (FIG. 16A-B).

Example 6. Human Clinical Trials Using a Topical Composition of Partially Differentiated hESC Membrane Extract A topical preparation was made by mixing stem cell membrane extract at 25% or 50% concentration in distilled water and a microbial inhibitor (phenoxyethanol and sorbic acid, 1%).

Other preparations used instead of water a cell culture media-based composition that has increased amino-acids concentration.

Figures 17A, 17B, 17C:
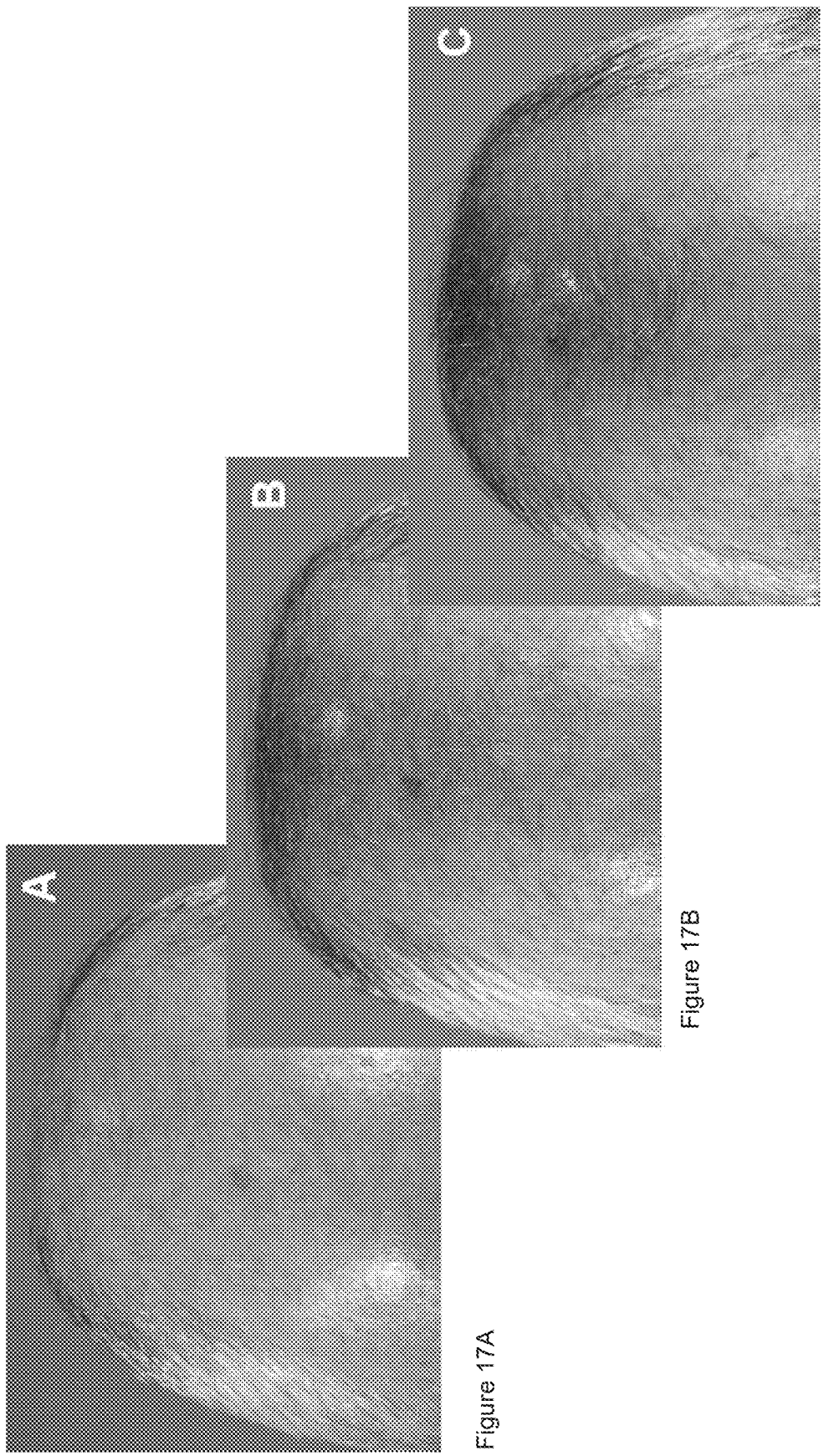
FIGS. 17A-C are a time series of photographs depicting the increasing growth of scalp hair with treatment with cell membrane extract. Specifically the images depict the scalp of a 65 year-old subject with Norwood-Hamilton VII baldness pattern exposed to a daily topical application demonstrating progressive accumulation of hair and regression to a type VI pattern or less, after 1 month (FIG. 17A), 1 months (FIG. 17B) and 4 months (FIG. 17C) from first application.
Figure 18B:
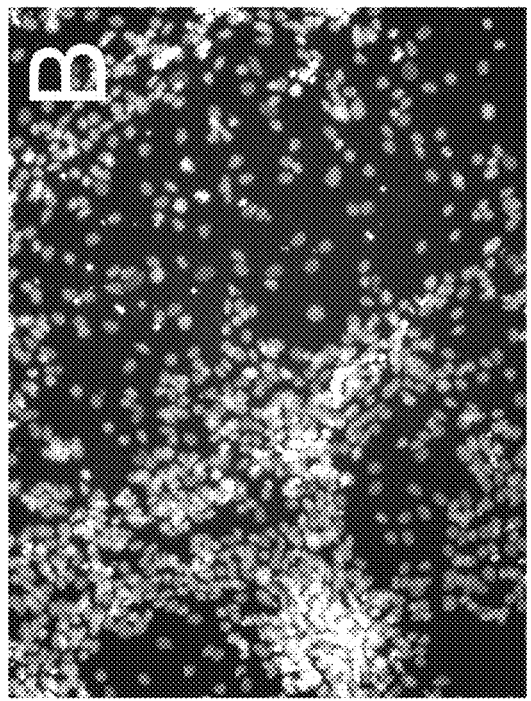
FIGS. 18A-D depict the immuno-cytochemical labeling for beta tubulin and nuclear (Hoechst) stain two weeks from thaw, of the cyclodextrin membrane extract-treated (FIGS. 18A and 18B) and control (FIGS. 18C and 18D) neural cultures (magnification 20×).
Figure 18D:
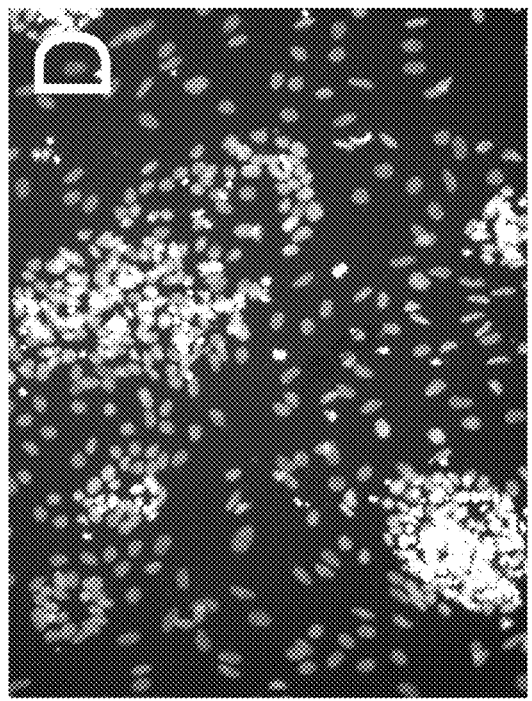
Figure 18A:
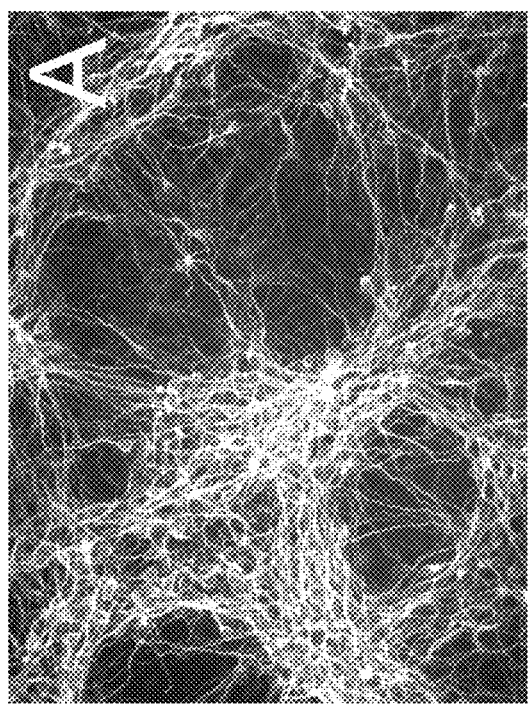
Figure 18C:
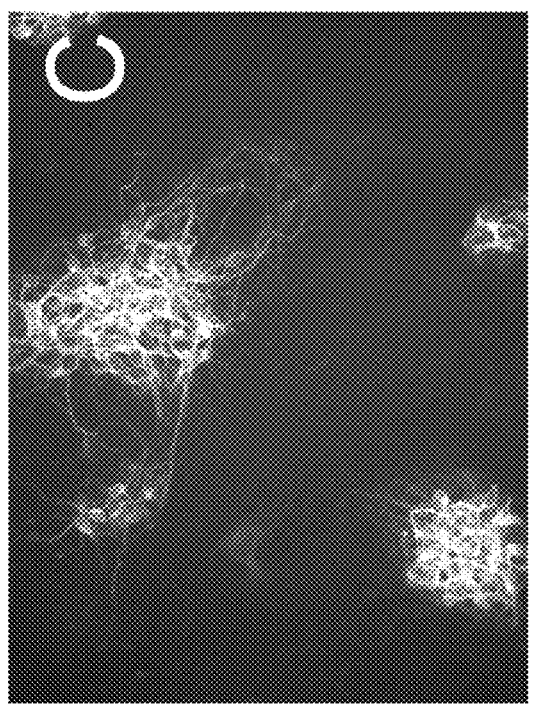
Figure 19B:
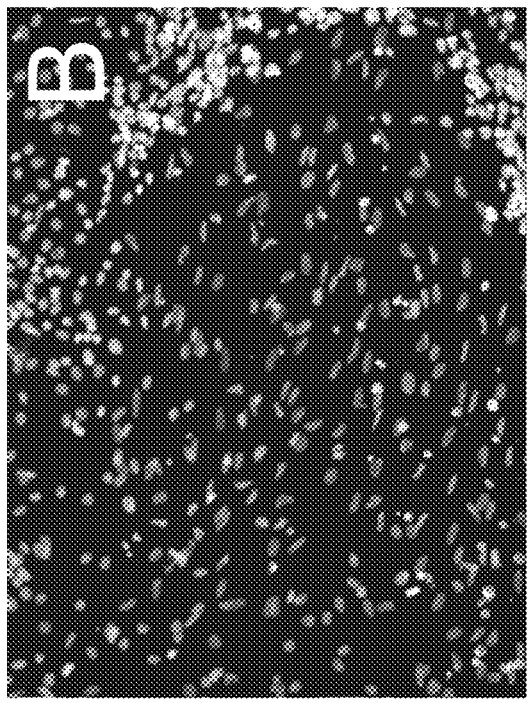
FIGS. 19A-D depict the immuno-cytochemical labeling for doublecortin and nuclear (Hoechst) stain two weeks from thaw, of the cyclodextrin membrane extract-treated (FIGS. 19A and 19B) and control (FIGS. 19C and 19D) neural cultures (magnification 20×).
Figure 19D:
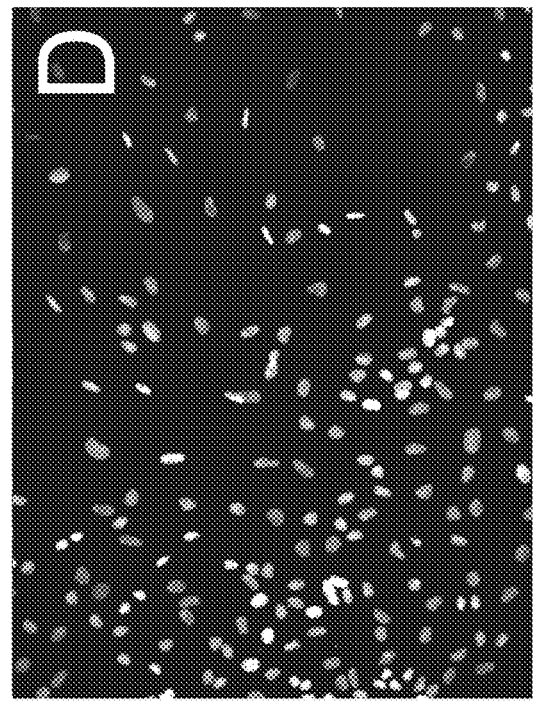
Figure 19A:
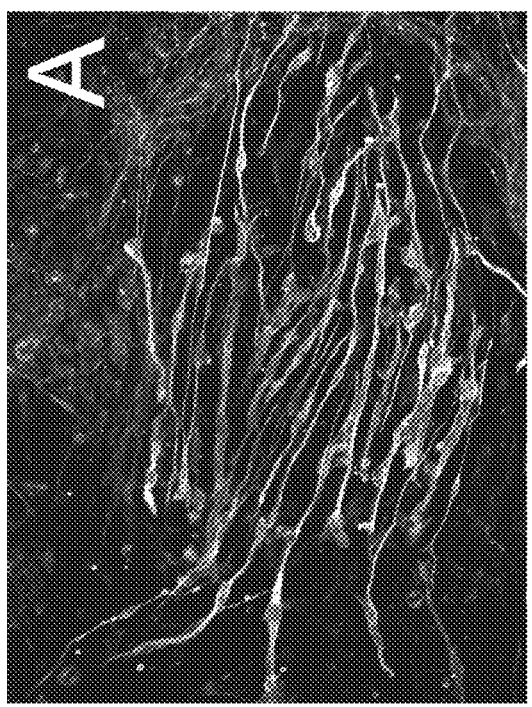
Figure 19C:
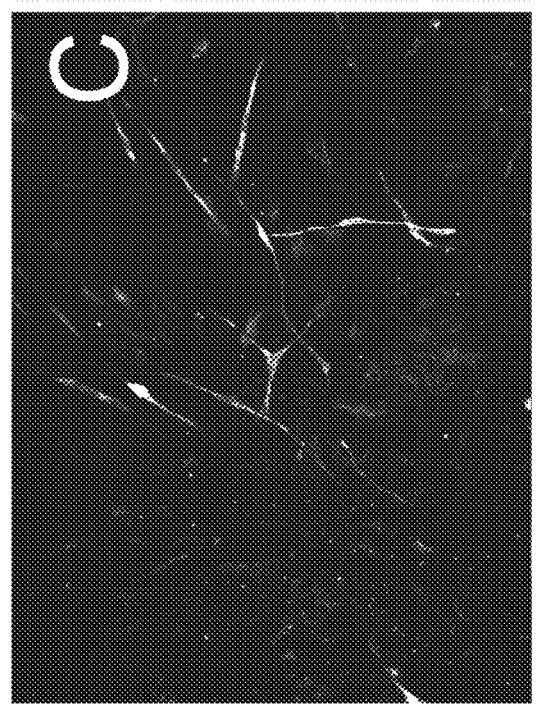

A human volunteer, a 65 years old male with Norwood-Hamilton type VII balding, was treated with the topical solution for 3 cycles of alternating 1-month daily application followed by one month of no application. Photographs in standardized conditions were taken after each treatment cycle. The images taken at 1 month apart prove the progressive accumulation of new hair after each treatment cycle and the regression to a type VI pattern or less, after 6 months from first application (FIG. 17).

A single-center clinical trial was conducted to assess the efficacy and tolerance of the hair growth treatment product when used in alternating courses as described below of 4 weeks each (16 weeks total followed by an 8-week regression period) in women and men with self-perceived thinning and shedding hair and clinically determined mild to moderate pattern hair loss (Ludwig I and II in women and Norwood III and IV in men).

A two-step treatment regimen was tested, using partially differentiated stem cell membrane extract with 10 mM methyl-beta-cyclodextrin and 20% trehalose in distilled water applied daily for four weeks, followed by another 4-week daily application of a topical composition comprising nutrients as found in cell culture media but that did not contain the membrane extract.

The study is designed with the following end-points:

Efficacy Endpoints

Investigator rating of standardized global photographs at weeks 4, 8, 12, and 16, and at week 24 following an 8-week regression period Subject rating of hair growth parameters at weeks 4, 8, 12, and 16, and at week 24 following an 8-week regression period Standardized global photographs of scalp taken at baseline and weeks 4, 8, 12, and 16, and at week 24 following an 8-week regression period Macrophotography of 1-cm-diameter area on scalp vertex performed at baseline and week 16 and 24, with image analysis for hair density and diameter performed after week 16 and 24 using images from baseline and weeks 16 and 24.

Subject-completed self-assessment questionnaires at baseline and weeks 4, 8, 12, and 16, and at week 24 following an 8-week regression period One 3-mm biopsy per subject taken at baseline and weeks 8 and 16 (total of 3 biopsies per subject), with samples shipped to Sponsor for analysis of histological improvement of scalp skin and hair follicle structure Efficacy is assessed through Investigator rating of standardized global photographs at weeks 4, 8, 12, and 16, and at week 24 following an 8-week regression period. Subjects rate hair growth parameters at weeks 4, 8, 12, and 16, and at week 24 following an 8-week regression period. Tolerability evaluations is performed at baseline and weeks 4, 8, 12, and 16, and at week 24 following an 8-week regression period, with weekly phone calls to subjects between baseline and week 4 to check for any AEs. Self-assessment questionnaires is completed at baseline and weeks 4, 8, 12, and 16, and at week 24 following an 8-week regression period. Standardized global photographs of scalp are taken at baseline and weeks 4, 8, 12, and 16, and at week 24 following an 8-week regression period. Macrophotography on scalp vertex are performed at baseline and weeks 16 and 24, with image analysis for hair density and diameter performed after week 16 and 24 study using images from both time points.

A biopsy (3 mm) is collected by the Study Dermatologist from each subject's scalp at baseline and weeks 8 and 16.

Safety/Tolerability Endpoints

Clinical grading of tolerance

Safety checks for adverse events (AEs)

Monitoring of AEs throughout the course of the study

At least 10 subjects meeting the eligibility requirements are expected to complete participation in the clinical trial, with at least 5 men and at least 5 women. Provided with the following instructions:

Use of the provided hair cleaning products at least 3 times per week.

Application:

Once daily, 2-3 drops of solution close to the hair roots. Spread evenly on entire scalp area and massage the product into the skin for about 1 minute.

On hair washing days, apply the product after the hair is washed (damp or dry). If hair is washed more than once a day, re-apply the product after each wash.

Leave on the product—it will dry clean with no residue.

Style as usual, avoiding the use of styling products (hairsprays, gels, etc.).

Tolerability evaluation is performed at baseline and follow-up time points. Local cutaneous tolerability is evaluated by assessing the signs of erythema, edema, and dryness/scaling, and by subject reporting of the degree of burning, stinging, and itching on the global scalp (treatment area).

Results:

After 8 weeks majority of the subject reported agreement or neutrality on positive outcome statements (see Table 7). Investigator evaluation revealed improvement on all parameters as shown in Table 8.

No adverse effects were reported by subjects or observed by the investigator.

TABLE 7

Subject self-assessment questionnaire showing the agreement of the majority of the subjects on improvement of hair 8 weeks after application

|  | evaluation at 4 week | | | Evaluation at 8 week | | |
| --- | --- | --- | --- | --- | --- | --- |
| Evaluated statement | Agree | Neutral | Disagree | Agree | Neutral | Disagree |
| Packaging is easy to use | 100% | 0% | 0% | 100% | 0% | 0% |
| Easy to apply | 90% | 7% | 10% | 100% | 0% | 0% |
| Makes hair styling easy | 73% | 36% | 0% | 64% | 27% | 9% |
| Does not leave residue | 91% | 0% | 9% | 91% | 0% | 9% |
| Appearance improved | 36% | 46% | 18% | 73% | 27% | 0% |
| Looks fuller/thicker | 46% | 46% | 9% | 73% | 27% | 0% |
| Scalp feels better | 46% | 55% | 0% | 55% | 46% | 0% |
| Less hair loss | 36% | 46% | 18% | 64% | 36% | 0% |
| Looks healthier | 46% | 55% | 0% | 64% | 36% | 0% |
| Looks stronger | 46% | 55% | 0% | 64% | 36% | 0% |
| Grew faster | 46% | 55% | 0% | 55% | 46% | 0% |

TABLE 8

Dermatologist evaluation of the subjects shows improvement of evaluated parameters as early as 4 weeks and continued improvement at 8 weeks.

| Evaluated parameter | Bbaseline score | Mean score at 4 weeks | Mean score at 8 weeks |
| --- | --- | --- | --- |
| Bald spot size improvement | 4 | 4.8 | 5.1 |
| Appearance of hair | 4 | 4.9 | 5.3 |
| Growth of hair | 4 | 4.9 | 5.5 |
| Slowing of hair loss | 4 | 4.4 | 5.5 |
| Satisfaction with hairline at the front of the head | 4 | 4.9 | 5.4 |
| Satisfaction with hair on top of the head | 4 | 5.2 | 5.4 |
| Satisfaction with hair overall | 4 | 4.9 | 5.2 |

Example 7. Neurotrophic Effect of Cells on Neural Cultures

Cryopreserved neural progenitors from day 14 of differentiation from embryonic stem cells were thawed and plated on laminin coated imaging cell culture slides at identical densities. A cyclodextrin membrane extract was added to some slides at 10 µL/mL v/v final concentration in the identical media to control. The cultures were maintained by replacing the media and addition of membrane extract 3 times per week for two weeks.

Two days after plating, in phase contrast microscopy, the control cultures show an initial loss of more differentiated neurons and overall reduction of the initial density. The cell recovery of the control plate was 42% at 48 hours. In contrast, a much better recovery of 85% at 48 hours was observed in the treated cultures. The cell morphology in the control plate displayed a trend of clumping of the neuronal cells surrounded by a higher number of the fibroblastic or epithelial cells. The treated plates presented a homogenously distributed neuronal morphology with much higher proportion to the epithelial or fibroblastic phenotype.

The cell culture was carried for two weeks replacing the media every two days in both conditions and adding 10 µL/mL cyclodextrin membrane extract to the treated. The slides were then fixed and stained for neuronal (beta III tubulin, doublecortin) and glial markers (GFAP). No glial cells were identified in any of the conditions.

The controls show islands of beta tubulin staining neurons surrounded by non-neuronal cells that expanded over the culture period. These neurons have limited (shorter and fewer) neurite outgrowth that don't expand beyond the cell agglomeration suggestive to a lack of maturation and trophic support of the culture condition The cultures exposed to cell membrane extract displayed extensive neurite outgrowth and homogenously distributed over the entire cell culture surface. The culture conditions facilitated the survival of the neurons the expansion of neurites and a proportional reduced number of beta tubulin negative cells. (see FIGS. 18A-D).

The treated cultures reveal doublecortin positive pockets demonstrating abundant presence of migratory neurons. In the control cultures only sporadic doublecortin positive cells can be observed (see FIGS. 19A-D).

Based on these experimental observations we conclude that the cyclodextrin membrane extract exercises the following effects on the neural tissue:
 a) Contribute to the survival of neuronal cells after exposure to a stressor factor (freeze/thaw cycle in this experiment)
 b) Enhanced morphological development as observed by robust neurite outgrowth positive for neurofilaments
 c) Persistence or expansion of young migratory neurons from the initial neural progenitors in the culture, positive for doublecortin
 d) No apparent proliferation enhancing effect on other cell types.

Neurodegenerative disorders can greatly benefit from the application of cyclodextrin-stem cell membrane extract complexes as a result of the enumerated mechanism of action by improved protection of the existing neurons and by improved neurogenesis. Such disorders include various forms of dementia, Alzheimer diseases, brain trauma, spinal cord injury and others. In addition, a beneficial effect is anticipated on peripheral nerve disorders that include various forms of peripheral neuropathy.

Unless otherwise indicated, all numbers expressing quantities of ingredients, properties such as molecular weight, reaction conditions, and so forth used in the specification and claims are to be understood as being modified in all instances by the term "about." As used herein the terms "about" and "approximately" means within 10 to 15%, preferably within 5 to 10%. Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein may be further limited in the claims using consisting of or consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed is:

1. A method of producing a composition comprising one or more cyclodextrin complexes of one or more lipid-modified proteins, wherein the one or more lipid-modified proteins are Wingless (Wnt), Hedgehog (Hh), or both, comprising:
   culturing one or more animal cells which are producing Wnt, Hh, or both proteins in a culture media;
   incubating the animal cells in a harvest solution comprising a cyclodextrin; and
   obtaining the cyclodextrin complex of the lipid-modified protein.

2. The method of claim 1, further comprising mixing the cyclodextrin complex of the lipid-modified protein with one or more pharmaceutically acceptable excipients to form a formulation.

3. The method of claim 1, wherein the harvest solution further comprises a kosmotrope.

4. The method of claim 3, wherein the kosmotrope is propylene glycol, proline, trehalose, ectoine, or trimethylamine N-oxide.

5. The method of claim 3, wherein the kosmotrope is present in the harvest solution at a concentration of about 5% w/v to about 30% w/v.

6. The method of claim 5, wherein the kosmotrope is present in the harvest solution at a concentration of about 20% w/v.

7. The method of claim 1, wherein the cyclodextrin is methyl cyclodextrin or hydroxypropyl-β-cyclodextrin.

8. The method of claim 1, wherein the cyclodextrin is present in the harvest solution at a concentration of about 1 mM to about 20 mM.

9. The method of claim 8, wherein the cyclodextrin is present in the harvest solution at a concentration of about 10 mM.

10. The method of claim 1, further comprising storing the cyclodextrin complex of the lipid-modified protein at 4° C. or lower.

11. The method of claim 1, further comprising lyophilizing the cyclodextrin complex of the lipid-modified protein.

12. The method of claim 2, wherein the one or more pharmaceutically acceptable excipients comprise one or more preservatives.

13. The method of claim 2, wherein the one or more pharmaceutically acceptable excipients comprise one or more antimicrobial agents.

14. The method of claim 1, wherein the Hh is Sonic Hedgehog (SHh) protein, a Desert Hedgehog (DHh) protein, an Indian Hedgehog (IHh) protein, or any combination thereof.

15. The method of claim 1, wherein the Wnt is Wnt3a, Wnt7b, Wnt10b, or any combination thereof.

16. The method of claim 1, wherein the one or more animal cells comprise a stem cell.

17. The method of claim 16, wherein the stem cell is an embryonic stem cell, parthenogenic stem cell, adult stem cell, fetal stem cell, or an induced pluripotent stem cell.

18. The method of claim 16, wherein the stem cell is genetically engineered to:
   a. overexpress Wnt, Hh, or both;
   b. be immortal; or
   c. express telomerase reverse transcriptase (hTERT).

19. The method of claim 1, further comprising administering the cyclodextrin complex of the lipid-modified protein to a subject in need thereof to promote tissue regeneration of a tissue.

20. The method of claim 19, wherein the tissue is epidermis, dermis, skin sensory receptors, skin appendages, hair, or nails.

21. The method of claim 1, further comprising administering the cyclodextrin complex of the lipid-modified protein to a subject in need thereof to treat a neurodegenerative disorder.

22. The method of claim 21, wherein the neurodegenerative disorder is Alzheimer's disease, Parkinson's disease, spinal cord injury, brain injury, peripheral nerve injury, peripheral neuropathy, multiple sclerosis, amyotrophic lateral sclerosis, or dementia.

23. The method of claim 1, further comprising administering the cyclodextrin complex of the lipid-modified protein to a subject in need thereof to treat a neuromuscular disorder.

24. The method of claim 23, wherein the neuromuscular disorder is myopathy, muscular dystrophy, or myasthenia gravis.

* * * * *